(12) United States Patent
Price et al.

(10) Patent No.: US 8,757,157 B2
(45) Date of Patent: Jun. 24, 2014

(54) MASK FOR DELIVERY OF RESPIRATORY THERAPY TO A PATIENT

(75) Inventors: Andrew Martin Price, Baulkham Hills (AU); Rupert Christian Scheiner, Davidson (AU); Philip Rodney Kwok, Chatswood (AU); Steven John Lubke, Stanmore (AU); Lee James Veliss, West Ryde (AU); Eva Ng, Double Bay (AU)

(73) Assignee: ResMed Limited, Bella Vista (AU)

( * ) Notice: Subject to any disclaimer, the term of this patent is extended or adjusted under 35 U.S.C. 154(b) by 1343 days.

(21) Appl. No.: 12/155,453

(22) Filed: Jun. 4, 2008

(65) Prior Publication Data

US 2009/0032026 A1 Feb. 5, 2009

Related U.S. Application Data

(60) Provisional application No. 60/935,268, filed on Aug. 2, 2007.

(51) Int. Cl.
*A61M 16/06* (2006.01)

(52) U.S. Cl.
USPC ............ 128/206.28; 128/206.21; 128/206.24; 128/207.11

(58) Field of Classification Search
USPC ............ 128/206.21, 206.24, 206.28, 207.11, 128/207.18, 206.27, 207.17; 24/200, 458, 24/522, 595.1, 666, 669; 2/417, 418, 421, 2/452, 183, 195.2, 195.4
See application file for complete search history.

(56) References Cited

U.S. PATENT DOCUMENTS

| | | | | | |
|---|---|---|---|---|---|
| 2,376,871 | A | * | 5/1945 | Fink | 128/201.19 |
| 4,574,799 | A | * | 3/1986 | Warncke | 128/206.24 |
| 4,739,755 | A | * | 4/1988 | White et al. | 128/206.12 |
| 4,782,832 | A | * | 11/1988 | Trimble et al. | 128/207.18 |
| 5,077,839 | A | * | 1/1992 | Keller | 2/421 |
| 5,724,965 | A | * | 3/1998 | Handke et al. | 128/207.13 |
| 6,112,746 | A | | 9/2000 | Kwok et al. | |
| 6,119,693 | A | | 9/2000 | Kwok et al. | |
| 6,374,826 | B1 | | 4/2002 | Gunaratnam et al. | |
| 6,439,230 | B1 | | 8/2002 | Gunaratnam et al. | |
| 6,532,961 | B1 | | 3/2003 | Gunaratnam et al. | |
| 6,581,594 | B1 | | 6/2003 | Drew et al. | |
| 6,702,792 | B2 | | 3/2004 | Nakamura et al. | |
| 6,907,882 | B2 | | 6/2005 | Ging et al. | |
| 7,121,279 | B2 | * | 10/2006 | Dennis | 128/206.21 |

(Continued)

FOREIGN PATENT DOCUMENTS

| | | |
|---|---|---|
| AU | 2005100738 | 9/2005 |
| WO | WO 2005/018524 | 3/2005 |

(Continued)

OTHER PUBLICATIONS

U.S. Appl. No. 60/848,360, filed Oct. 2006, Lubke et al.

*Primary Examiner* — Jackie T Ho
*Assistant Examiner* — Kathryn E Ditmer
(74) *Attorney, Agent, or Firm* — Nixon & Vanderhye P.C.

(57) ABSTRACT

A mask for delivery of respiratory therapy to a patient may include one or more of the following improvements: rigidizer provided to headgear strap, locking clip/clip receptacle headgear connection, keyed headgear buckles, lotion dispenser on frame, rotatable prongs to adjust orientation, alignment indicators provided to prong, cushion and/or frame, chin flap with bellows arrangement, vent holes positioned away from gas entry port, and vent holes to direct washout gas at an angle.

29 Claims, 32 Drawing Sheets

(56) References Cited

U.S. PATENT DOCUMENTS

| | | |
|---|---|---|
| 7,188,620 B2 | 3/2007 | Amarasinghe |
| 7,216,647 B2 | 5/2007 | Lang et al. |
| 7,318,437 B2 | 1/2008 | Gunaratnam et al. |
| 2002/0053347 A1* | 5/2002 | Ziaee ................. 128/207.18 |
| 2003/0145859 A1* | 8/2003 | Bohn et al. ........... 128/206.24 |
| 2003/0196656 A1 | 10/2003 | Moore et al. |
| 2003/0196658 A1* | 10/2003 | Ging et al. ........... 128/201.22 |
| 2004/0118406 A1 | 6/2004 | Lithgow et al. |
| 2006/0076019 A1* | 4/2006 | Ho ..................... 128/206.24 |
| 2006/0124131 A1 | 6/2006 | Chandran et al. |
| 2006/0174887 A1* | 8/2006 | Chandran et al. ..... 128/206.11 |
| 2007/0144525 A1 | 6/2007 | Davidson et al. |
| 2007/0272249 A1* | 11/2007 | Chandran et al. ..... 128/206.28 |
| 2007/0295338 A1* | 12/2007 | Loomas et al. ........ 128/207.18 |

FOREIGN PATENT DOCUMENTS

| | | |
|---|---|---|
| WO | WO 2005063328 A1 * | 7/2005 |
| WO | PCT/AU2006/001095 | 8/2005 |
| WO | PCT/AU2006/000037 | 1/2006 |
| WO | PCT/AU2006/000770 | 6/2006 |
| WO | WO 2006/074513 | 7/2006 |
| WO | PCT/AU2006/001507 | 10/2006 |
| WO | WO 2007/045008 | 4/2007 |

* cited by examiner

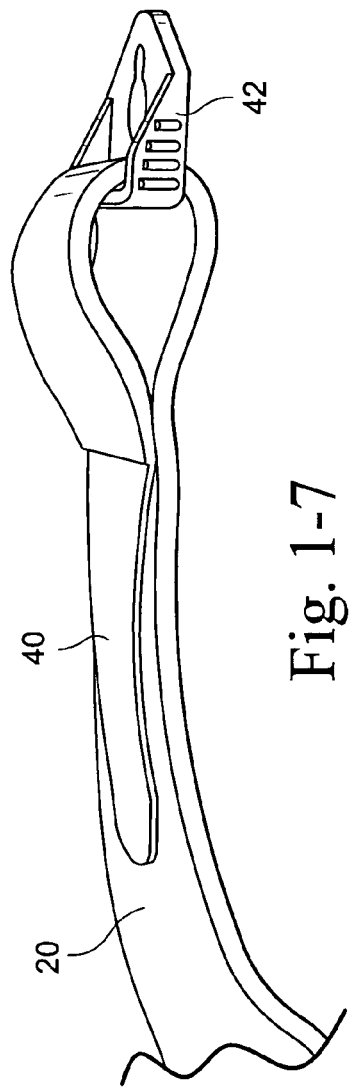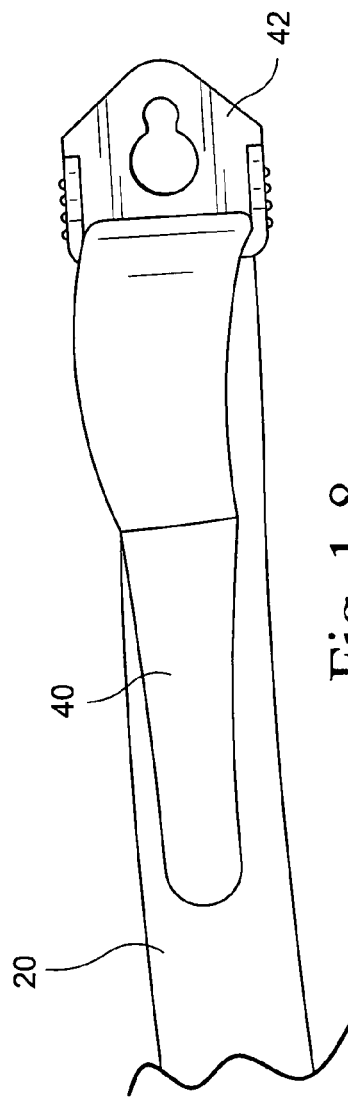
Fig. 1-7 (PRIOR ART)
Fig. 1-8 (PRIOR ART)

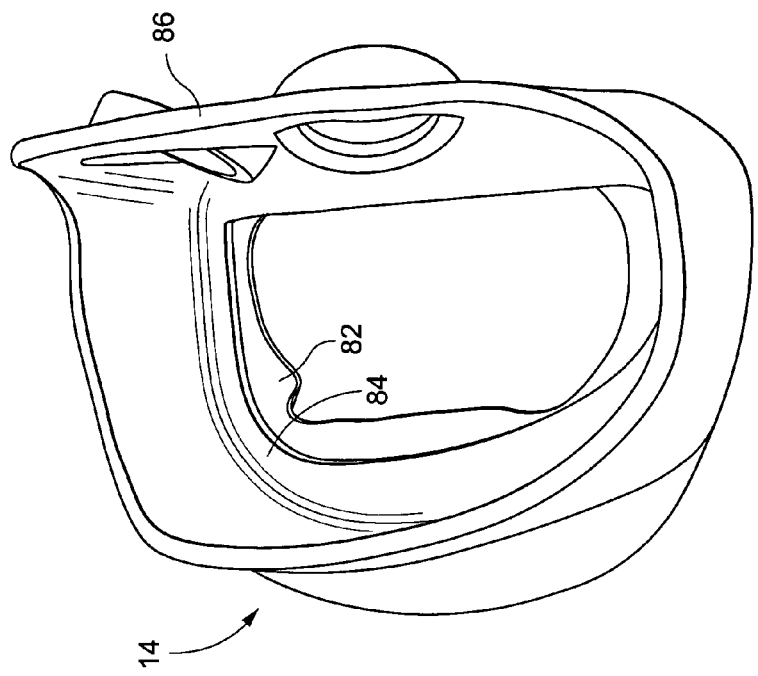
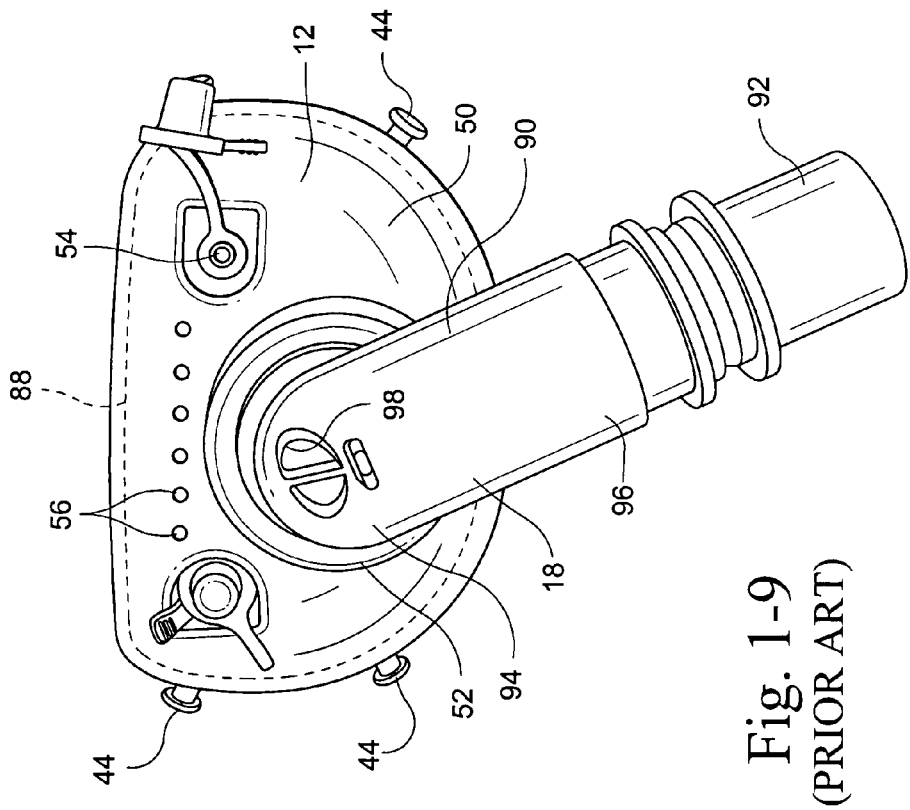
Fig. 1-10
(PRIOR ART)
Fig. 1-9
(PRIOR ART)

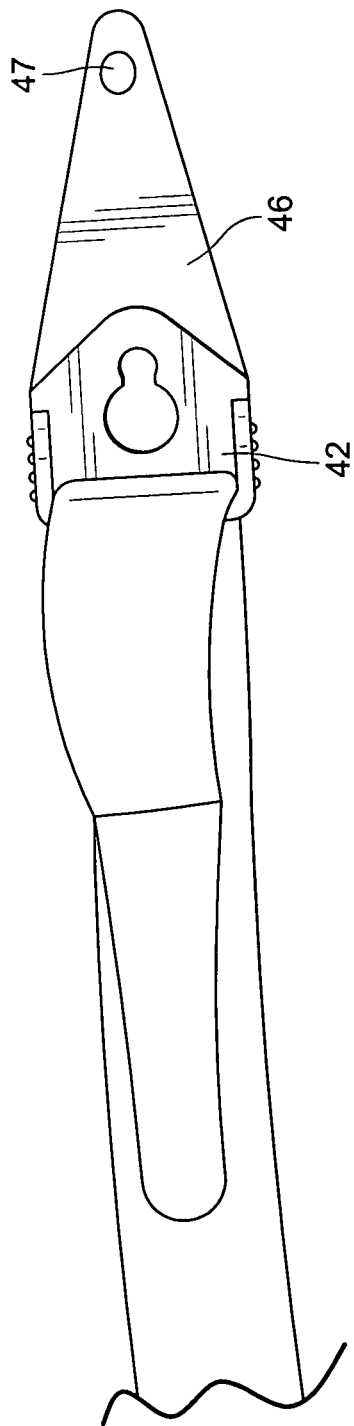
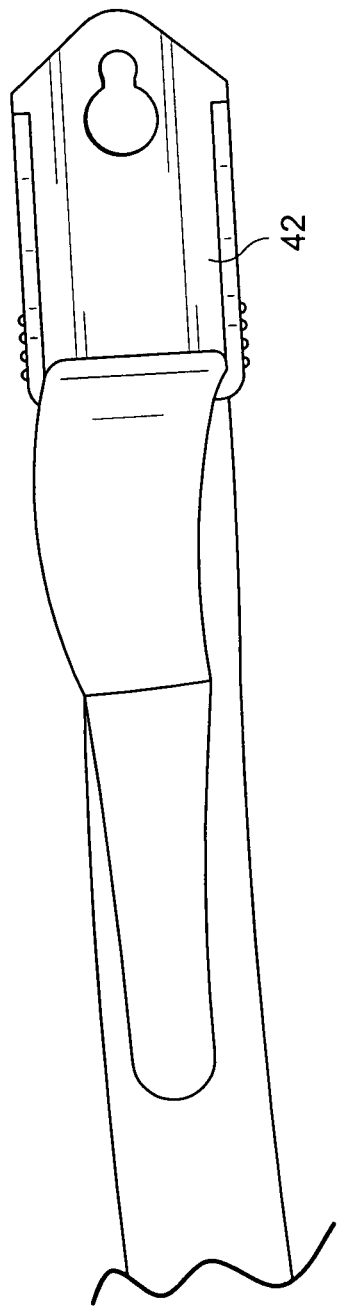
Fig. 3-1
Fig. 3-2

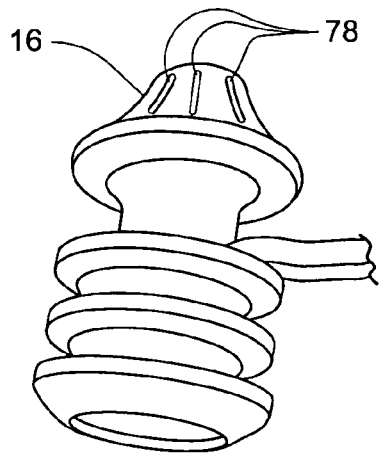
Fig. 5-8
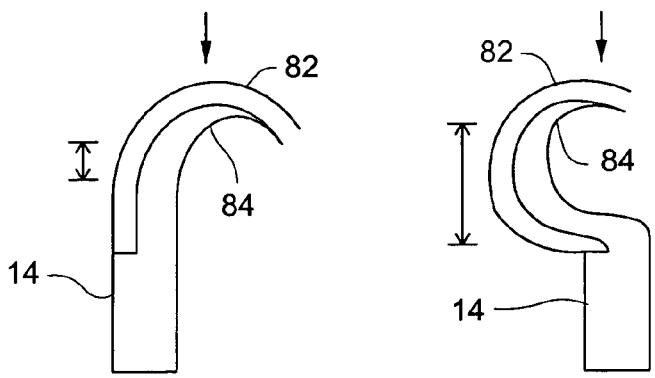
Fig. 6-1-1 (PRIOR ART)
Fig. 6-1-2
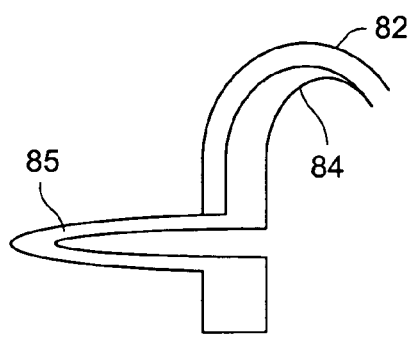
Fig. 6-2

MASK FOR DELIVERY OF RESPIRATORY THERAPY TO A PATIENT

CROSS-REFERENCE TO APPLICATION

This application claims the benefit of U.S. Provisional Application No. 60/935,268, filed Aug. 2, 2007, which is incorporated herein by reference in its entirety.

FIELD OF THE INVENTION

The present invention relates to a mask for delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) such as Obstructive Sleep Apnea (OSA).

BACKGROUND OF THE INVENTION

A known mask is commercially sold under the name of HYBRID™ by Respcare, Inc. and one or more portions of the mask are described in U.S. Patent Publication No. 2006/0124131, published Jun. 15, 2006, and/or at the website www.hybrid-mask.com.

SUMMARY OF THE INVENTION

One aspect of the present invention relates to improvements and/or alternative arrangements of HYBRID™ mask to enhance respiratory therapy.

Another aspect of the invention relates to a mask including a frame, a facial and nasal interface provided to the frame, and headgear provided to the frame to maintain the mask in a desired position on the patient's face. The headgear includes at least one strap and a buckle provided to the strap. The buckle includes an opening adapted to engage a post provided on the frame. The opening and/or the post includes a keyed portion structured to prevent rotation of the buckle with respect to the post when the buckle is engaged with the post.

Another aspect of the invention relates to a mask including a frame, a facial and nasal interface provided to the frame, and a lotion dispenser or moisturizer provided to frame and adapted to dispense lotion for lubricating and/or moisturizing the facial and/or nasal interface.

Another aspect of the invention relates to a mask including a frame, a cushion provided to the frame and adapted to form a seal around an exterior of the patient's mouth in use, and nasal prongs provided to the cushion and adapted to from a seal with the patient's nasal passages in use. Each of the nasal prongs is adapted to rotate relative to the cushion to change the angle at which the nasal prong extends with respect to the cushion.

Another aspect of the invention relates to a mask including a frame, a cushion provided to the frame and adapted to form a seal around an exterior of the patient's mouth in use, and a chin portion or chin flap provided to the cushion and adapted to engage the patient's chin in use. The chin portion or chin flap includes a bellows arrangement structured to allow movement of the patient's chin in use.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIGS. 2-1 to 2-9 illustrate headgear according to alternative embodiments of the present invention;

FIGS. 3-1 to 3-4 illustrate headgear connection according to alternative embodiments of the present invention;

FIGS. 4-1 to 4-2 illustrate frames according to alternative embodiments of the present invention;

FIGS. 5-1 to 5-2 illustrate nasal prongs according to alternative embodiments of the present invention;

FIG. 5-3-1 illustrates a nasal prong of the HYBRID™ mask;

FIGS. 5-3-2 and 5-3-3 illustrate a nasal prong according to an embodiment of the present invention;

FIGS. 5-4 to 5-8 illustrate nasal prongs according to alternative embodiments of the present invention;

FIG. 6-1-1 illustrates a cushion profile of the HYBRID™ mask;

FIG. 6-1-2 illustrates a cushion profile according to an embodiment of the present invention;

FIGS. 6-2 to 6-3 illustrate cushions according to alternative embodiments of the present invention;

FIGS. 7-1 to 7-3 illustrate elbow assemblies according to alternative embodiments of the present invention; and FIGS. 8-1 to 8-4 illustrate vent arrangements according to alternative embodiments of the present invention.

DETAILED DESCRIPTION OF ILLUSTRATED EMBODIMENTS

Figure 1:
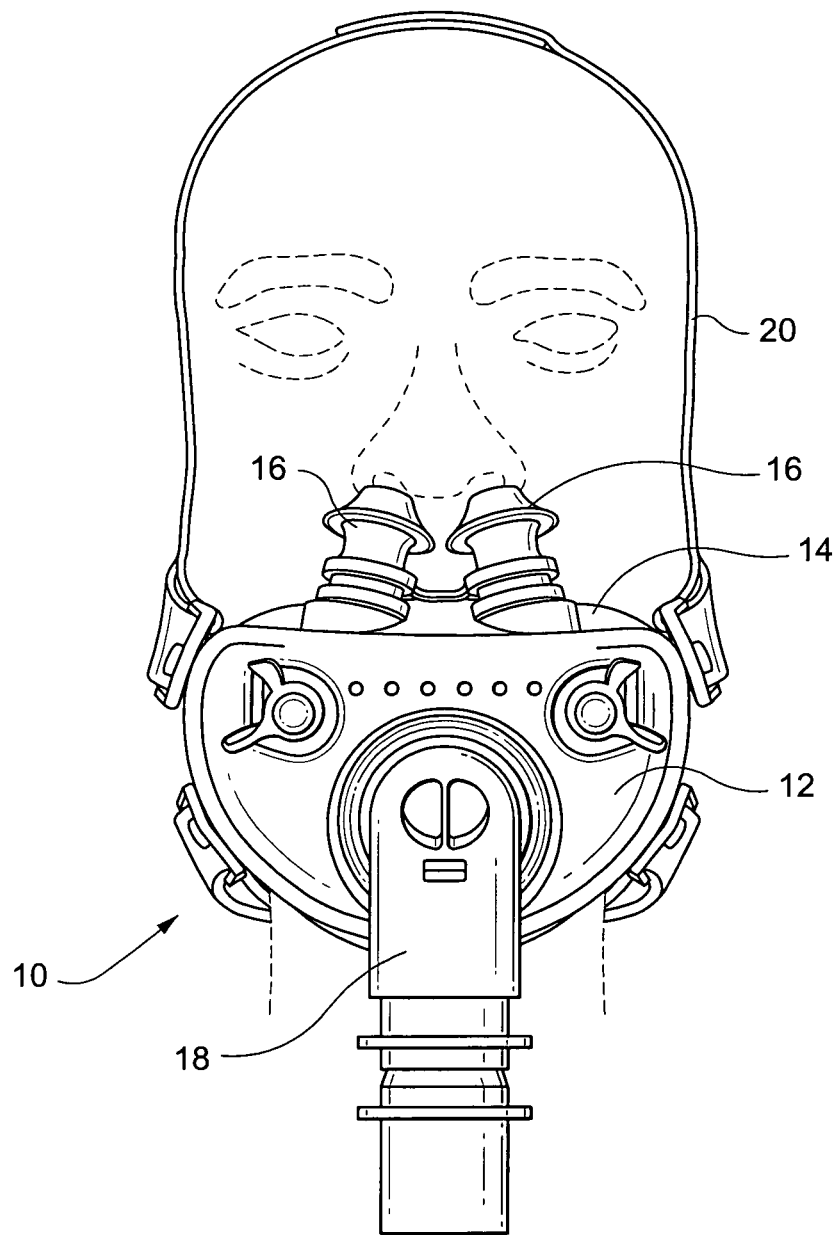
FIGS. 1-1 to 1-12 are various views of a known mask commercially sold under the name of HYBRID™.

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Each illustrated embodiment includes features that may be adapted for use and/or incorporated into the embodiments and/or components of the HYBRID™ mask, the mask described in U.S. Patent Publication No. 2006/0124131, published Jun. 15, 2006, and/or at the website www.hybrid-mask.com, as would be apparent to those of ordinary skill in the art. The HYBRID™ mask, U.S. Patent Publication No. 2006/0124131, and the website www.hybrid-mask.com are each incorporated herein by reference in its entirety.

While each illustrated embodiment is described as being implemented into a HYBRID™ mask, a mask of the type described in U.S. Patent Publication No. 2006/0124131, and/or a mask of the type described at the website www.hybrid-mask.com, each illustrated embodiment may be implemented into other masks, e.g., full-face mask, mouth mask, nasal mask, nasal prongs, nozzles, nare seals, and/or cannulae.

1. Known Mask

FIGS. 1-1 to 1-12 illustrate a known mask 10 commercially sold under the name of HYBRID™ and one or more portions of the mask are described in U.S. Patent Publication No. 2006/0124131 and/or at the website www.hybrid-mask.com. As illustrated, the mask 10 includes a ventilation interface or frame 12, a cushioned facial interface or cushion 14 provided to the frame 12 and adapted to form a seal around an exterior of the patient's mouth in use, a nasal interface or nasal prongs or nasal pillows 16 provided to the cushion 14 and adapted to from a seal with the patient's nasal passages or nares in use, an elbow assembly 18 provided to the frame 12 and adapted to be connected to an air delivery tube that delivers breathable gas to the patient, and headgear 20 removably attached to the frame 12 to maintain the mask 10 in a desired position on the patient's face.

2. Improvements to Known Mask

The following embodiments describe improvements and/or alternative arrangements of the HYBRID™ mask to enhance respiratory therapy.

2.1 Headgear

The headgear 20 of the HYBRID™ mask is constructed of a soft, flexible material and includes upper side straps 22 that pass over the patient's ear's, lower side straps 24 that pass below the patient's ear's, a Velcro® adjustable overhead strap 26 that passes over the top of the patient's head, and upper and lower rear straps 28, 29 that pass behind the patient's head and neck (e.g., see FIGS. 1-1, 1-2, and 1-6).

2.1.1 Rigid Element

Figures 1, 2:
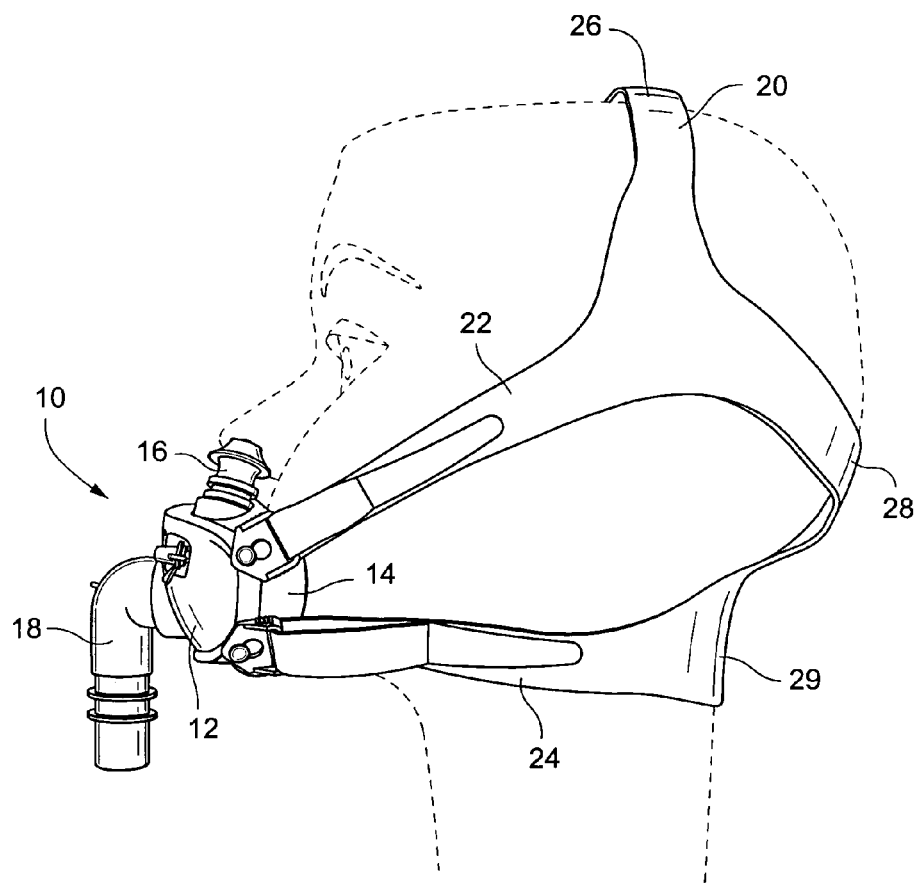

In an alternative embodiment, as shown in FIG. 2-1, a rigid element or rigidizer 30 may be provided to each upper side strap 22 and/or each lower side strap 24 to improve stability of the mask 10 on the patient's face, e.g., vertical stability. In addition, the rigid element 30 may be structured to orient force vectors in the correct direction to provide comfortable sealing. The rigid element 30 may be constructed of a rigid or semi-rigid material, e.g., nylon or plastic, and may be attached to the strap 22, 24 in any suitable manner, e.g., stitching, welding, gluing, or mechanically fixed.

Exemplary embodiments of such a rigid element provided to a headgear strap is disclosed in U.S. Pat. No. 6,907,882 and U.S. application Ser. No. 10/781,929, filed Feb. 20, 2004, each of which is incorporated herein by reference in its entirety.

2.1.2 Velcro® Removal

In an alternative embodiment, as shown in FIG. 2-2, the Velcro® adjustment on the overhead strap 26 may be removed and the respective headgear strap portions attached to one another, e.g., sewn together, to create a one size fits all headgear. This arrangement may simplify headgear adjustment.

An exemplary embodiment of such headgear is disclosed in PCT Application No. PCT/AU2006/000770, filed Jun. 6, 2006, which is incorporated herein by reference in its entirety.

2.1.3 Lower Rear Strap Positioning

Figures 1, 2, 3:
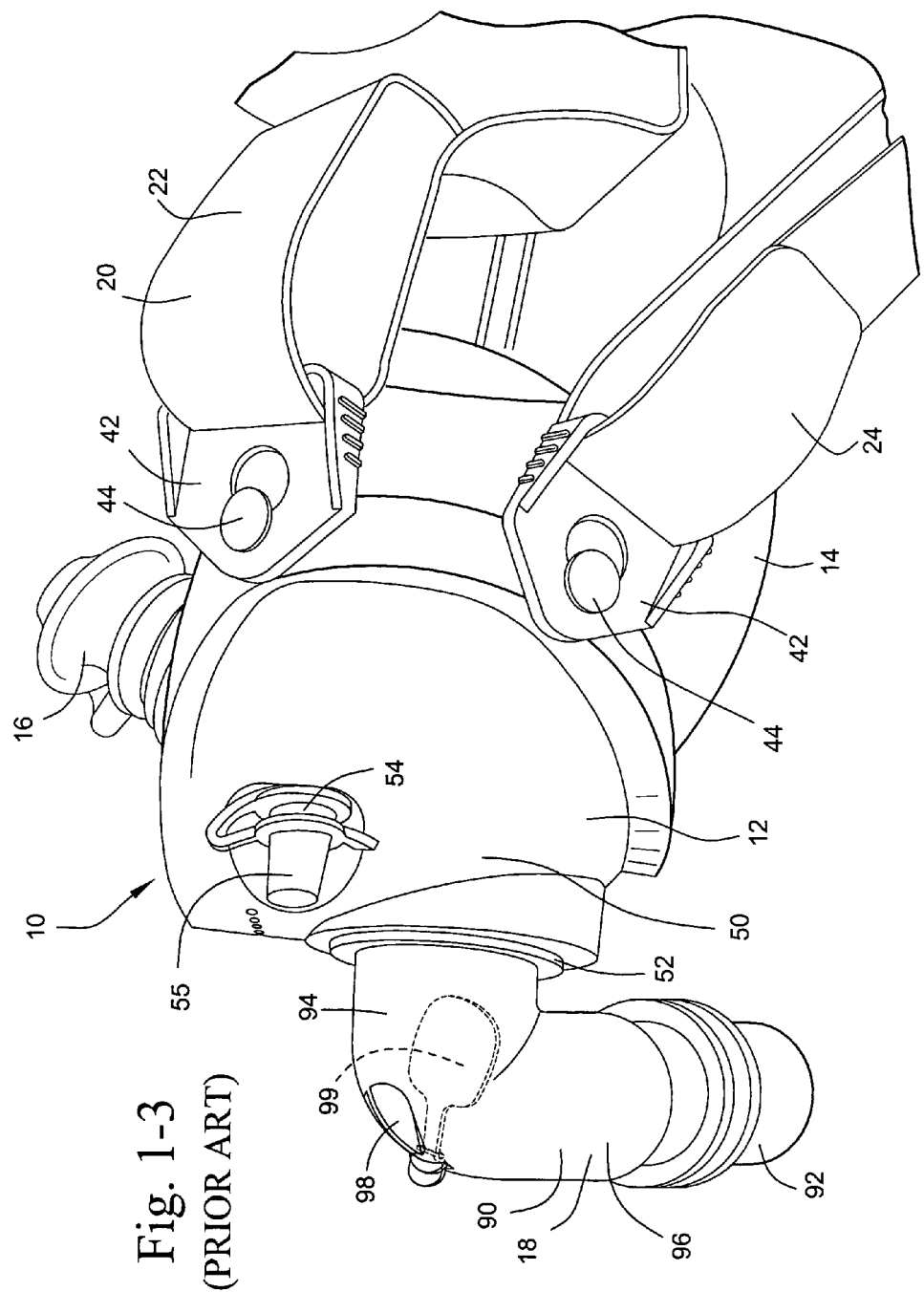

In an alternative embodiment, the lower rear strap 29 (see FIG. 1-6) that passes behind the patient's neck may be moved from that location. That is, the lower rear strap 29 may be arranged to pass behind a lower portion of the patient's head and above the patient's neck, as shown in FIG. 2-3. This arrangement would prevent the mask from pulling off in use, e.g., when the patient looks upwards.

An exemplary embodiment of such lower strap arrangement is disclosed in U.S. patent application Ser. No. 10/433,779, filed Nov. 13, 2003, which is incorporated herein by reference in its entirety.

2.1.4 Other Headgear Alternatives

In an alternative embodiment, one or more of the headgear straps may be constructed of a more elastic material, e.g., the upper and/or lower side straps 22, 24.

Figures 1, 2, 3, 4:
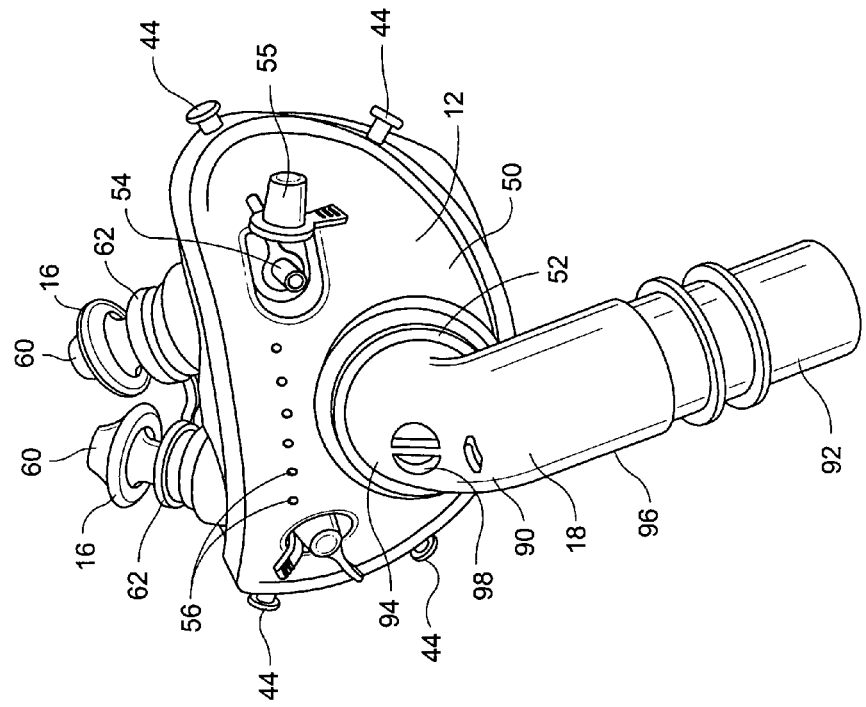

In another alternative embodiment, Velcro® joints may be incorporated into one or more straps of the headgear 20 so that different parts of the headgear 20 could be aligned in different ways. For example, Velcro® joints 31 may be incorporated into the upper and/or lower rear straps 28, 29 to allow adjustment of the length and/or angle of the upper and/or lower rear straps 28, 29 as shown in FIG. 2-4.

In another alternative embodiment, the upper side straps 22 and/or the upper rear strap 28 may be configured such that there is more space between the strap and the patient's ears, e.g., move upper side straps 22 away from the patient's ears as shown in FIG. 2-5.

In another alternative embodiment, one or more straps of the headgear 20 may include a relatively soft cover, sock, or pad, e.g., constructed or foam or gel, to improve comfort and/or aesthetics. The cover, sock, or pad may be attachable and retrofitable to the headgear straps. In an embodiment, the cover, sock, or pad is especially provided near the patient's eyes and/or cheeks. For example, FIG. 2-6 illustrates covers 33 provided to portions of the upper and lower side straps 22, 24.

In another alternative embodiment, as schematically shown in FIG. 2-7, the headgear 20 may include a pair of side straps 32 adapted to connect to the frame 12, and each side strap 32 forks into upper and lower side straps 22, 24 such as those described above.

In another alternative embodiment, an outrigger may be incorporated into the headgear 20 and/or frame 12 to help stabilize the frame 12 on the patient's face.

In another alternative embodiment, as shown in FIG. 2-8, the headgear strap vectors may be changed, e.g., move lower side straps 24 up towards upper side straps 22 to change strap vector of lower side straps 24. In an embodiment, the strap vectors may be adjustable such as those described in U.S. Pat. No. 6,907,882, which is incorporated herein by reference in its entirety.

In another alternative embodiment, as shown in FIG. 2-9, a strap or sling 34 may be attached to the frame 12 and adapted to engage the patient's nose, e.g., nasal bridge region or tip, to prevent downward movement of the mask in use.

2.2 Headgear Connection

The upper and lower side straps 22, 24 of the HYBRID™ headgear 20 each include a Velcro® tab 40 that engages the remainder of the strap 22, 24 to secure a buckle 42 in place. Each buckle 42 is adapted to engage a respective post 44 (e.g., mushroom-shaped post) on the frame 12 to secure the headgear 20 to the frame 12. Specifically, each buckle 42 is interlocked with a respective post 44 by first moving the buckle 42 adjacent the respective post 44 such that the respective post 44 extends through a larger opening in the buckle 42, and then moving the buckle 42 into engagement with the post 44 to interlock the post 44 with a smaller opening in the buckle 42 (e.g., see FIGS. 1-3, 1-7, and 1-8).

2.2.1 Quick Release

In an alternative embodiment, as shown in FIG. 3-1, a quick release rip-cord mechanism, extension member, or finger tab 46 may be provided on the end of one or more of the buckles 42 to facilitate engagement and/or disengagement of each buckle 42 with the respective post 44 on the frame 12. The finger tab 46 may be rigid or flexible. In use, the finger tab 46 may be pulled to move the respective post 44 into the larger opening in the buckle 42, thereby allowing quick release or disengagement of the buckle 42 from the respective post 44. That is, the finger tab 46 allows the buckle 42 to be levered out of the respective post 44. In an embodiment, the free end of the finger tab 46 may include a ball-like protrusion 47 to facilitate grip.

An exemplary embodiment of such a finger tab is disclosed in U.S. patent application Ser. No. 10/584,711, filed Jun. 26, 2006, which is incorporated herein by reference in its entirety.

2.2.2 Extended Buckle

In an alternative embodiment, as shown in FIG. 3-2, the buckles 42 provided to the upper and/or lower side straps 22, 24 may be extended in length to improve stability of the mask 10 on the patient's face.

2.2.3 Locking Clip and Clip Receptacle

In an alternative embodiment, the buckle/post headgear connection of the HYBRID™ mask 10 may be replaced by locking clips, e.g., spring-loaded clip, adapted to engage respective clip receptacles provided to the frame. Exemplary clip arrangements are described in PCT Application No. PCT/AU2006/000770, filed Jun. 6, 2006, and U.S. Pat. Nos. 6,374,826 and 6,907,882, each of which is incorporated herein by reference in its entirety.

In an embodiment, the locking clip may be configured to lock into at least one configuration or direction, e.g., lockable angular adjustment.

In another embodiment, each side of the frame may include only one clip/receptacle headgear connection (e.g., use with headgear shown in FIG. 2-7).

In another embodiment, the locking clip and/or clip receptacle may include a ratcheting arrangement to allow indexed rotational adjustment.

In another embodiment, the clip receptacle regions of the frame may be constructed of a malleable material to allow the clip receptacles to be positioned at different angles. In yet another embodiment, the clip receptacle regions of the frame may include a lockable ball joint to provide limited movement of the clip receptacles.

2.2.4 Other Headgear Connection Alternatives

In an alternative embodiment, the buckle and/or post may be keyed to prevent rotation of the buckle when attached to the post. This arrangement will maintain the headgear straps in a particular orientation or direction. For example, FIG. 3-3 illustrates a buckle 42 wherein the smaller opening includes a keyed portion 35 that is adapted to interlock with a keyed post 37 provided to the frame, thereby allowed the buckle 42 to rotate and lock into a desired position.

In an alternative embodiment, a peg or post may be provided on a headgear strap that is adapted to engage within a respective hole provided to the frame.

In an alternative embodiment, a press-button quick release mechanism may be incorporated into the headgear connection, e.g., such as that described in Australian Patent Application No. AU 2005100738 A4, filed Sep. 8, 2005, which is incorporated herein by reference in its entirety.

In an alternative embodiment, a spring-biased pull tab quick release mechanism may be incorporated into the headgear connection.

In an alternative embodiment, as shown in FIG. 3-4, a rotatable buckle 45 may be coupled to both upper and lower side straps 22, 24. The buckle 45 may engage a keyed post 49 having protrusions 51 adapted to engage with corresponding recesses 48 in the buckle 45 and provide indexed incremental rotational adjustment.

2.3 Frame

The frame 12 of the HYBRID™ mask 10 includes a main body 50 having a gas entry port 52 adapted to connect to the elbow assembly 18. The frame 12 also includes supplemental oxygen ports 54, vent holes 56, and posts 44 adapted to engage buckles 42 provided to the headgear 20 (e.g., see FIGS. 1-3 to 1-5 and 1-9).

2.3.1 Frame Alternatives

In an alternative embodiment, as shown in FIG. 4-1, the frame 12 may include a lotion dispenser (e.g., pocket) or moisturizer 58, e.g., positioned between the prongs 16 in use.

The lotion dispenser or moisturizer 58 may be adapted to dispense lotion for lubricating and/or moisturizing the prongs 16 and/or the cushion 14.

In an alternative embodiment, as shown in FIG. 4-2, the frame 12 may include one or more chin grabbing flaps 59. The one or more chin grabbing flaps may be retrofit to the frame 12. The one or more chin grabbing flaps may be elastic to improve fit and/or seal of the cushion 14, or the one or more chin grabbing flaps may be configured to stop jaw-drop.

2.4 Prongs

The nasal prongs or nasal pillows 16 of the HYBRID™ mask 10 each include a single-wall head portion 60 adapted to provide a seal with the patient's nasal passage and a base portion 62 adapted to be mounted to the cushion 14. The base portion 62 is formed with rings 64 defining at least one groove 66 therebetween. The cushion 14 includes two portals 68 that define flanges adapted to engage a respective groove 66 to secure the prong 16 in position (e.g., see FIGS. 1-4, 1-5, 1-11, and 1-12).

2.4.1 Dual Wall Prongs

Figures 1, 2, 3, 4, 5:
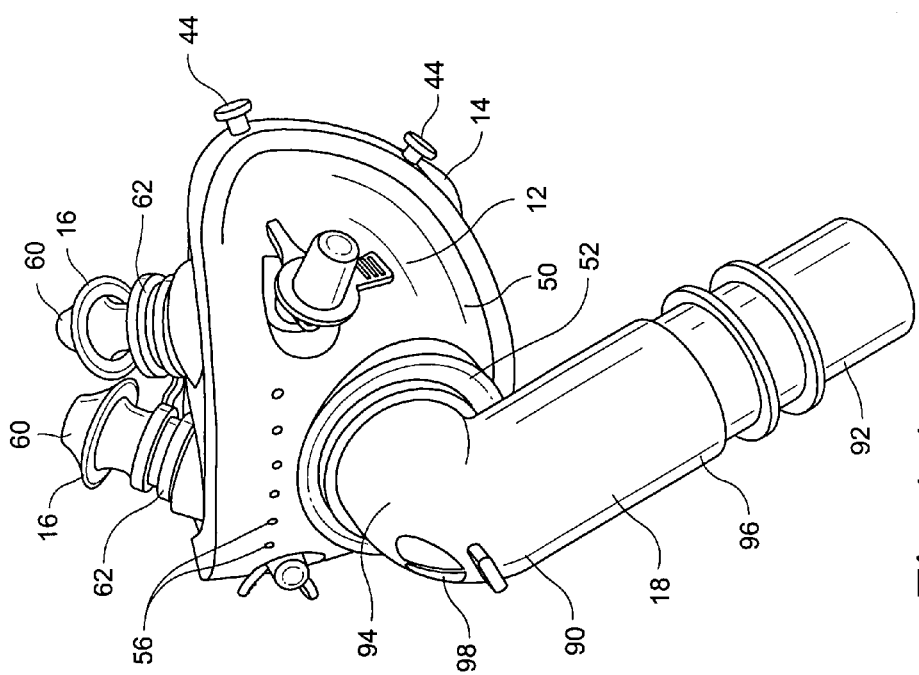

In an alternative embodiment, as shown in FIG. 5-1, each nasal prong 16 may include a dual or double wall head portion 60 (e.g., inner and outer walls 61, 63) to enhance the seal of the head portion 60 against the patient's nare. An exemplary dual wall nasal prong is described in U.S. patent application Ser. No. 10/584,711, filed Jun. 26, 2006, and PCT Application No. PCT/AU2006/000770, filed Jun. 6, 2006, each of which is incorporated herein by reference in its entirety.

In another alternative embodiment, the head portion 60 of each prong may include more than two walls, e.g., three or more walls.

2.4.2 Trampoline-Like Base

In an alternative embodiment, each nasal prong 16 may include a trampoline-like base portion. Specifically, as shown in FIG. 5-1, the wall section within the grooves 66 may be thinned, e.g., thinned silicone, and the connecting bar 65 joining the prongs 16 may removed or cut to allow each nasal prong 16 to rotate and/or articulate about the base portion (as indicated by the arrows). An exemplary trampoline-like base is described in U.S. patent application Ser. No. 10/584,711, filed Jun. 26, 2006, and PCT Application No. PCT/AU2006/000770, filed Jun. 6, 2006, each of which is incorporated herein by reference in its entirety.

2.4.3 Alignment Indicators

In an alternative embodiment, one or more alignment indicators may be added to the prongs 16 and/or cushion 14 to aid alignment of the prongs 16 with respect to the cushion 14. For example, alignment indicators 75 may be provided to the prongs 16 (see FIG. 5-7) that are adapted to be aligned with respective alignment indicators 77 provided to the cushion 14 (see FIG. 6-3). An exemplary alignment indicator is also described in U.S. Provisional Patent Application No. 60/848,360, filed Oct. 2, 2006, which is incorporated herein by reference in its entirety.

2.4.4 Prong Angle

In an alternative embodiment, the prong 16 may be configured to extend at different prong angles as the prong 16 is rotated. For example, as schematically shown in FIG. 5-2, the prong 16 may include a cam arrangement or leveling device including an sloped end 70 that is adapted to engage a sloped base 72, e.g., provided to the cushion 14. When the prong 16 is rotated, the sloped end 70 moves relative to the sloped base 72 which changes the angle at which the prong 16 extends.

As shown in FIG. 5-3-1, the grooves 66 in each HYBRID™ prong 16 are aligned with a horizontal axis of the prong 16. In another alternative embodiment, one or more grooves 66 in the base portion of the prong 16 may be configured to position the prong 16 at an angle. For example, as shown in FIG. 5-3-2, a groove 66A may be sloped with respect to a horizontal axis of the prong 16 which is adapted to position the prong 16 at an angle when mounted to the cushion 14 (see FIG. 5-3-3).

2.4.5 Other Prong Alternatives

In an alternative embodiment, the wall thickness of each prong may be reduced, e.g., to about 0.5 mm.

In an alternative embodiment, each prong 16 may be rotatable relative to the cushion 14, and the prong rotation may include indexing or incremental stops.

In an alternative embodiment, as shown in FIG. 5-4, each prong 16 may have a drinking straw style concertina configuration 74 along its stalk and/or base portion to provide angle adjustment of the prong 16. Such an arrangement is disclosed in U.S. patent application Ser. No. 10/584,711, filed Jun. 26, 2006, which is incorporated herein by reference in its entirety.

In an alternative embodiment, as shown in FIG. 5-5, each prong 16 may have one or more detents 76 to provide relatively large angle adjustment of the prong 16.

In an alternative embodiment, the base of each prong 16 may include a gimble or universal joint for adjustment.

In an alternative embodiment, each prong 16 may have a preload to provide a sealing force with the patient's nare.

In an alternative embodiment, one or more of the rings 64 at the base portion of each prong 16 may be sized such that the prong 16 cannot push through the respective portal in the cushion 14. For example, FIG. 5-6 illustrates a prong 16 wherein the uppermost rings 64 are sufficiently larger than the portals in the cushion 16.

Figures 1, 2, 3, 4, 5, 6:
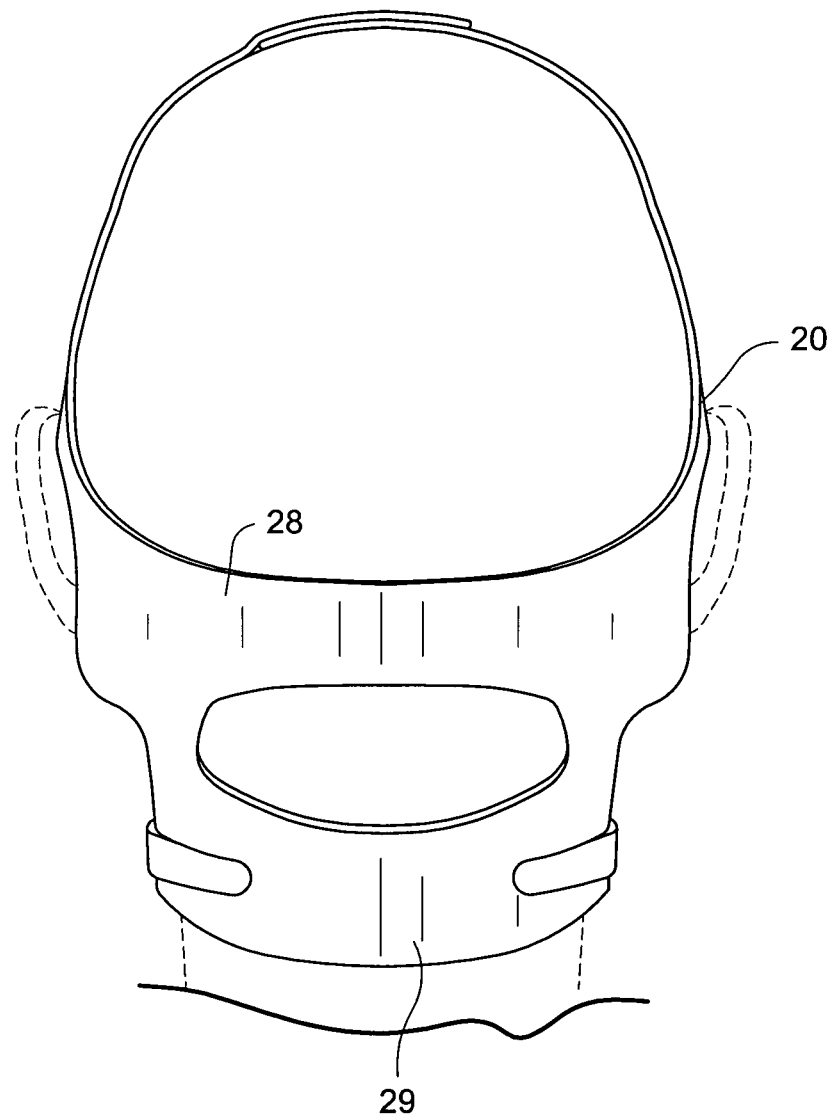
Figures 1, 2, 3, 4, 5, 6, 7, 8, 9, 10, 11:
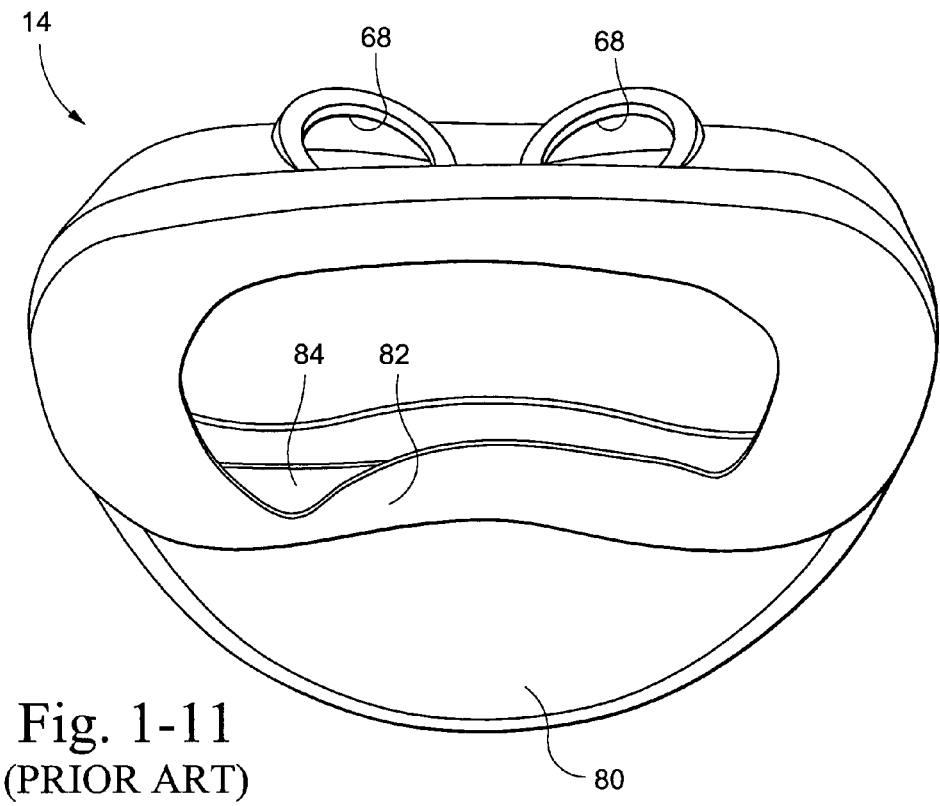
Figures 1, 2, 3, 4, 5, 6, 7, 8, 9, 10, 11, 12:
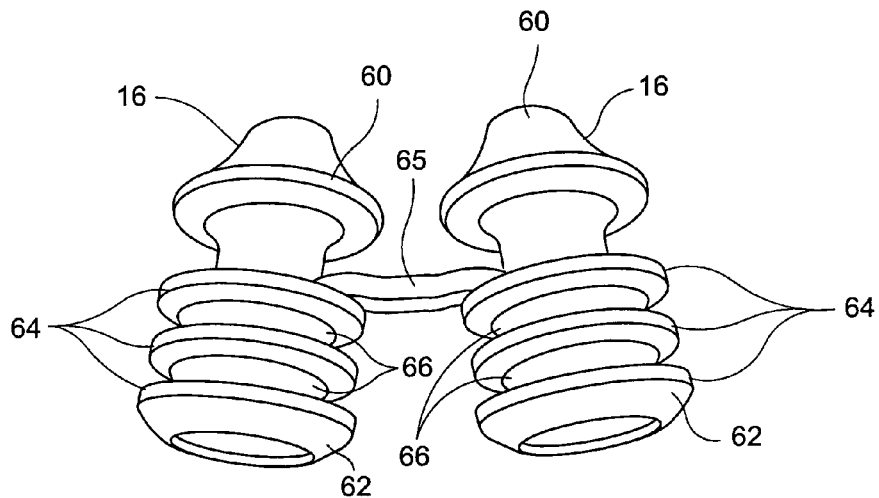
Figures 1, 2:
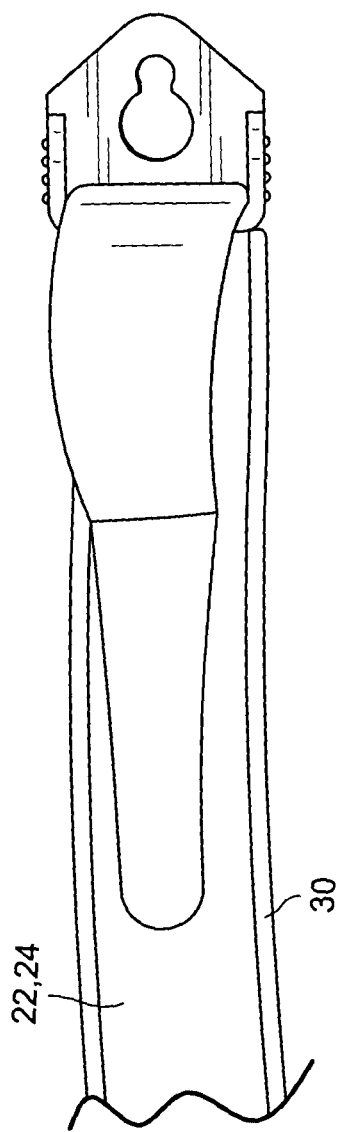
Figure 2:
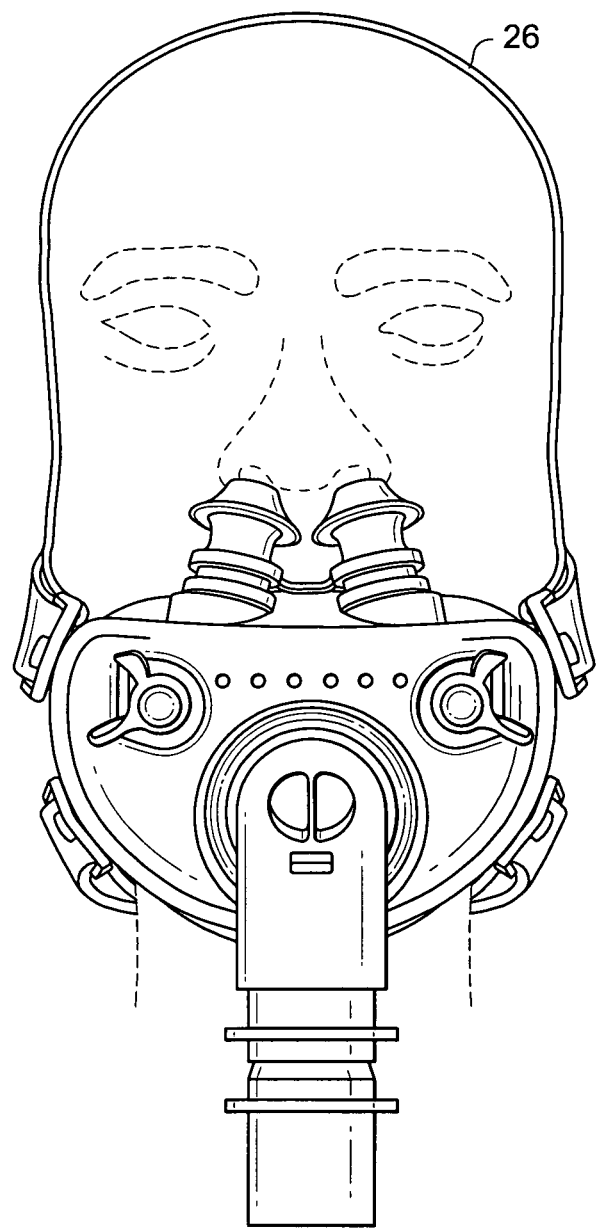
Figures 2, 3:
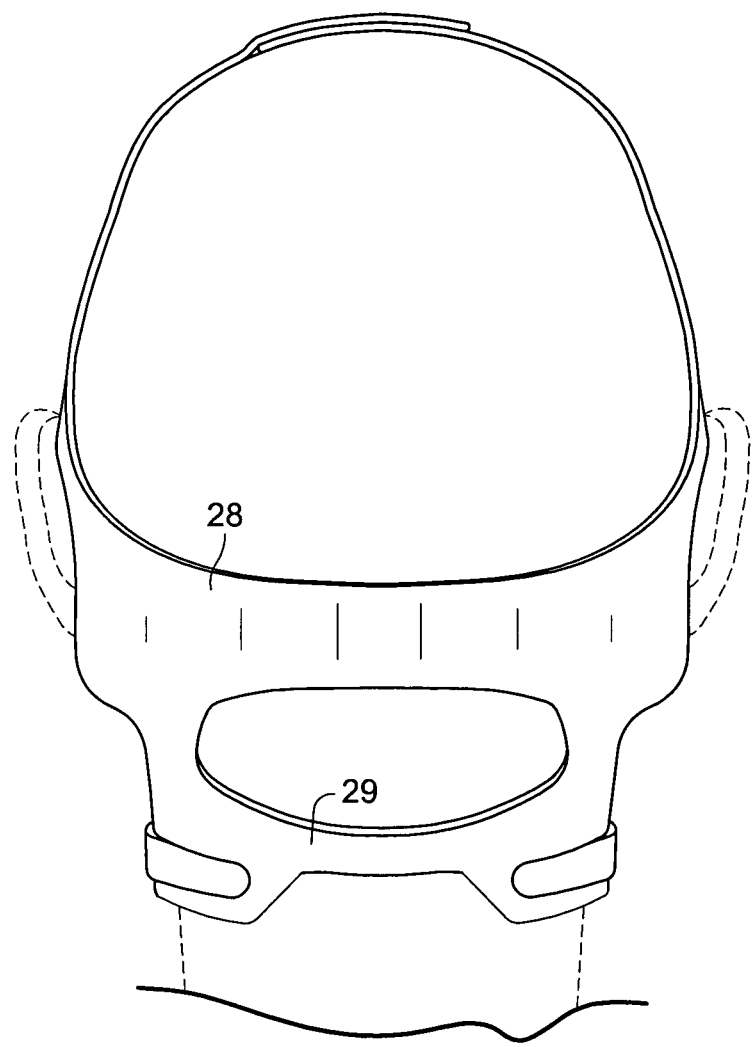
Figures 2, 3, 4:
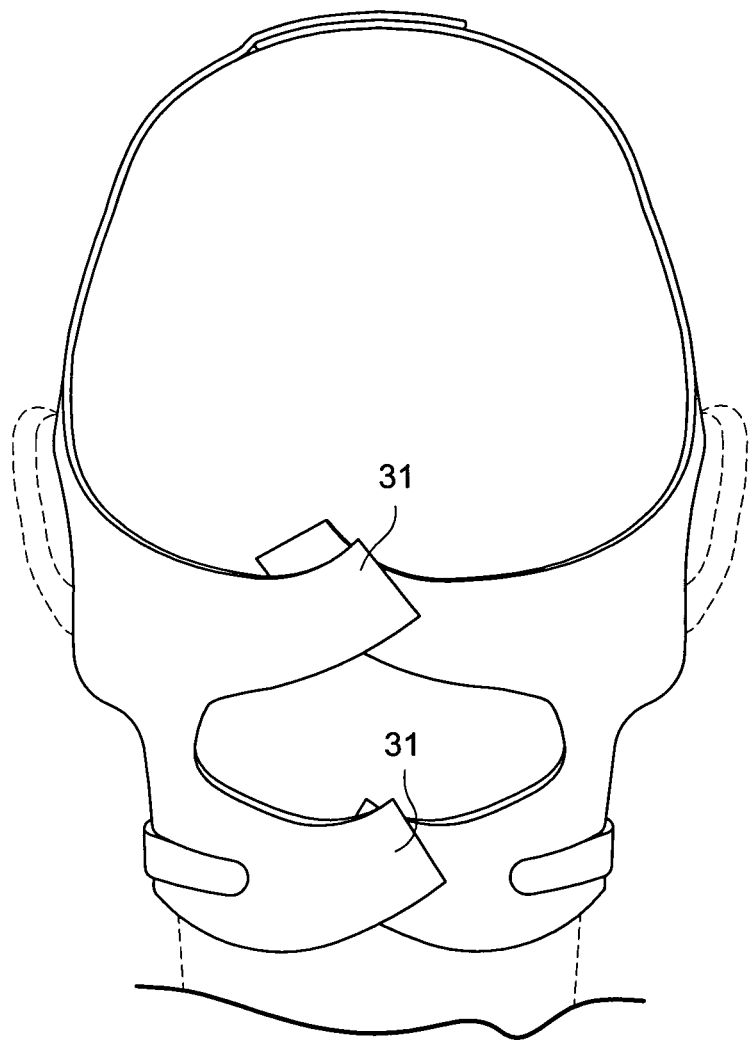
Figures 2, 3, 4, 5:
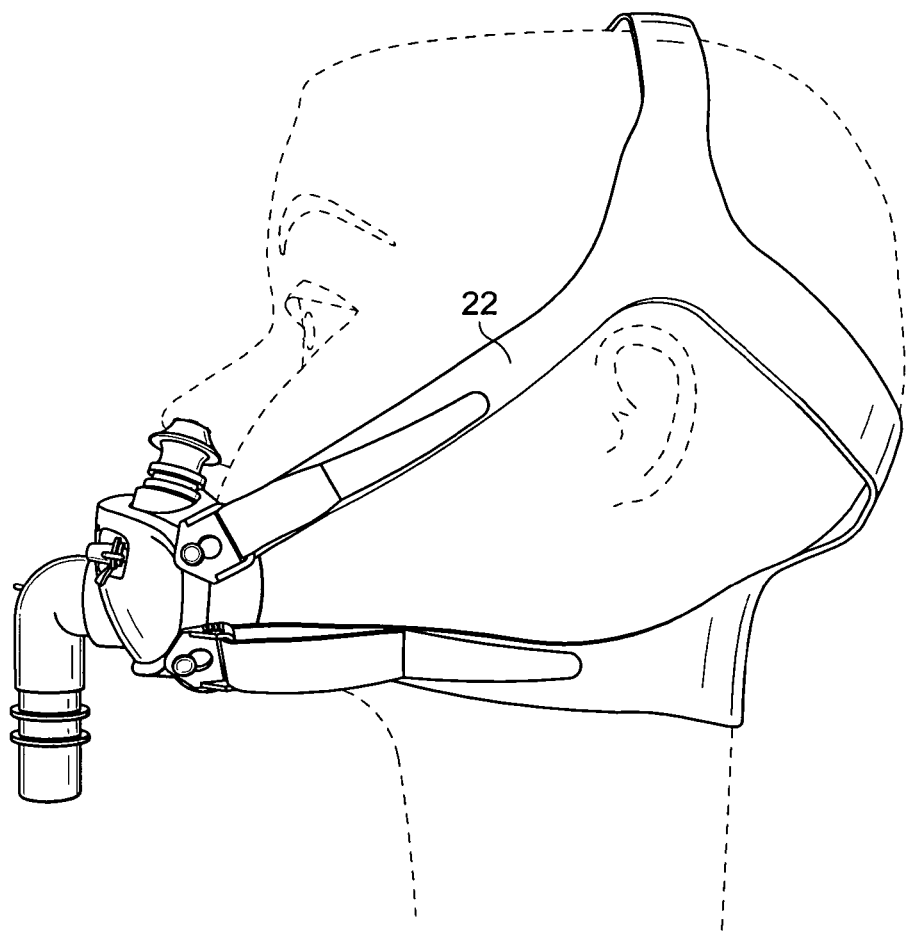
Figures 2, 3, 4, 5, 6:
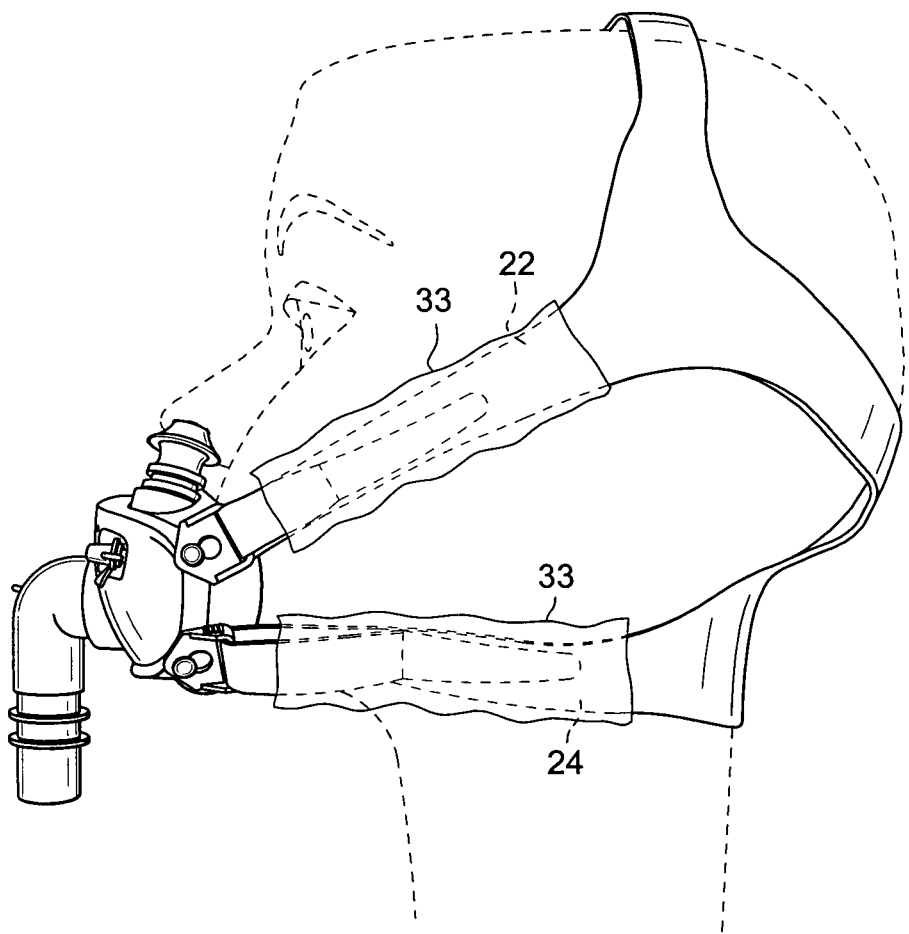
Figures 2, 3, 4, 5, 6, 7:
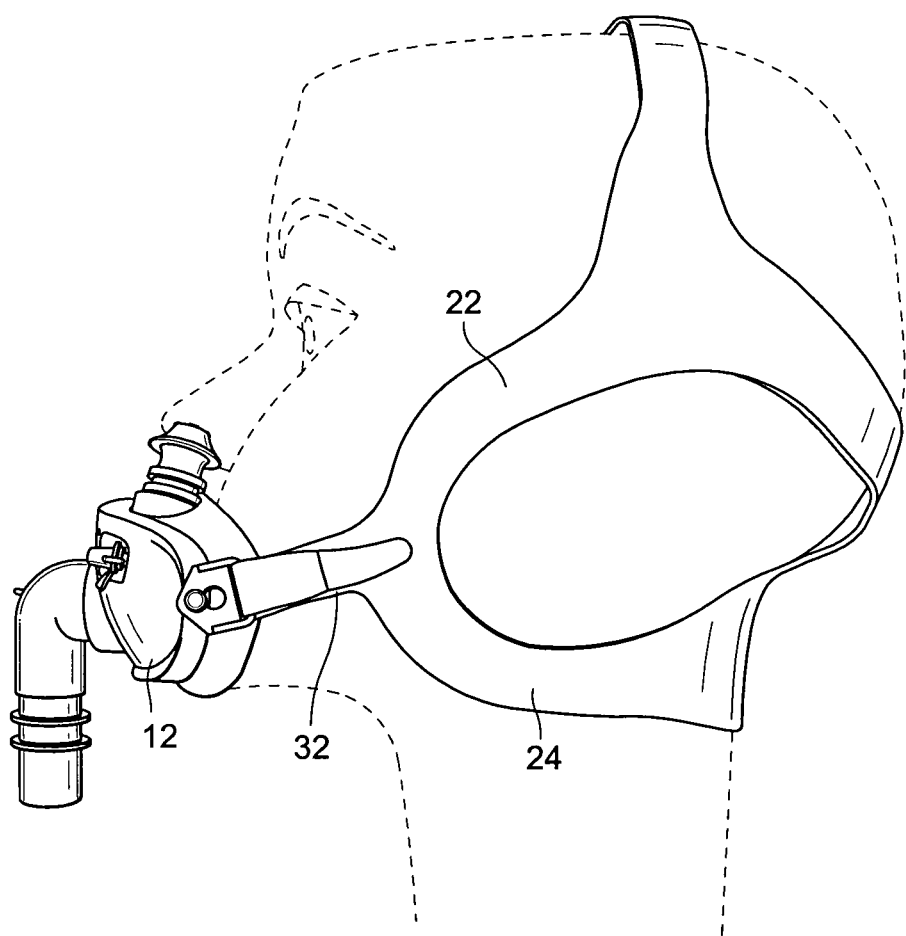
Figures 2, 3, 4, 5, 6, 7, 8:
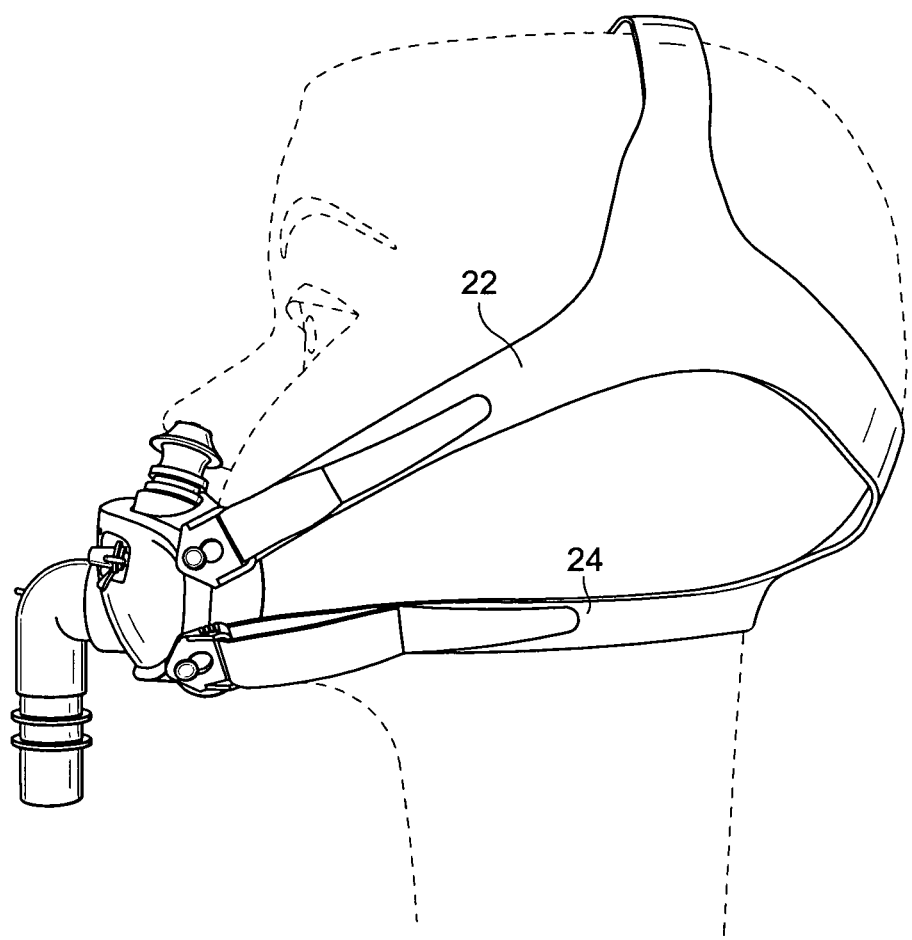
Figures 2, 3, 4, 5, 6, 7, 8, 9:
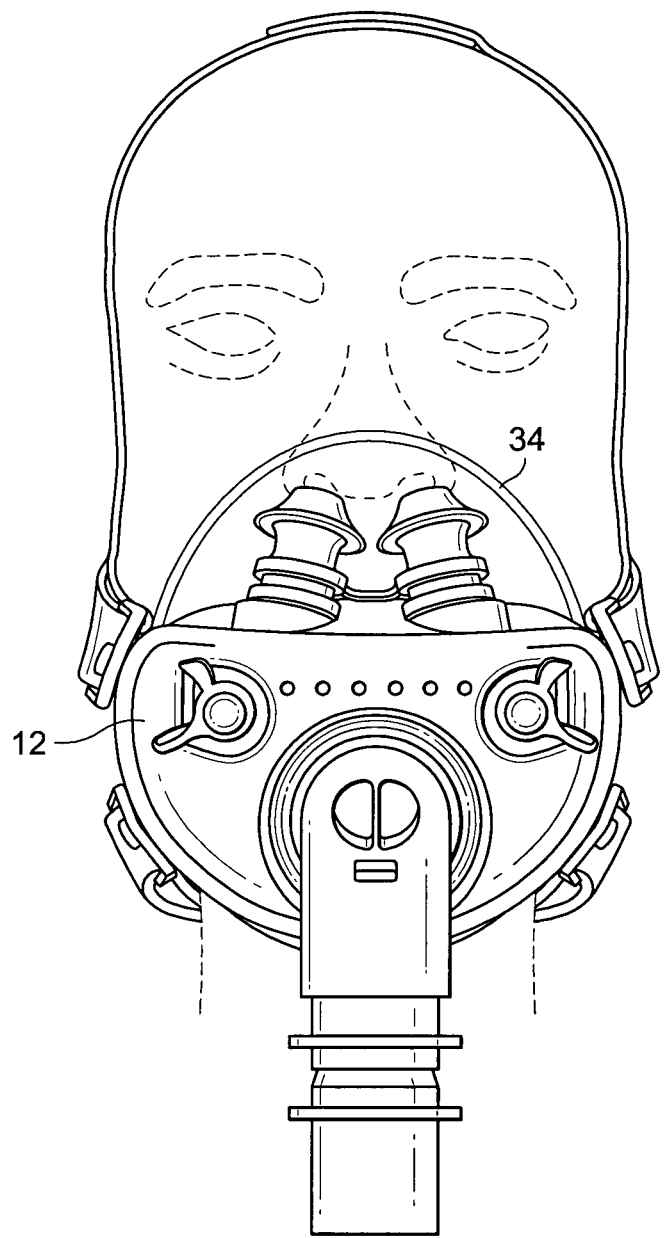
Figure 3:
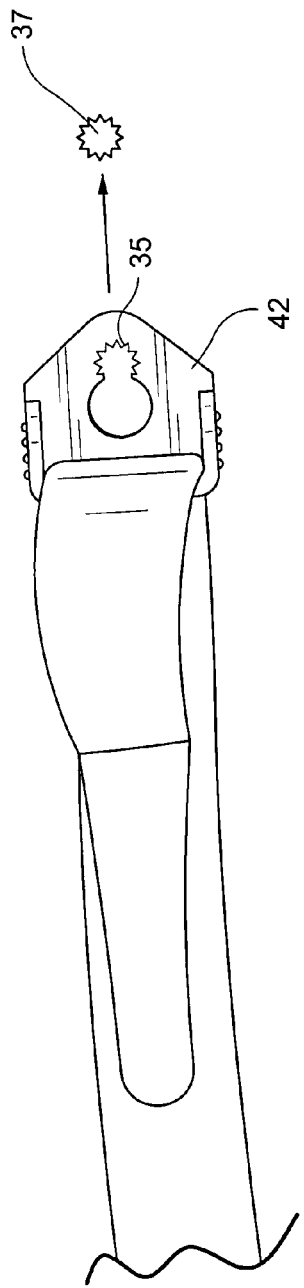
Figures 3, 4:
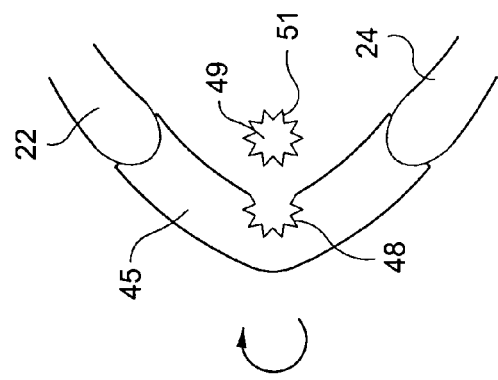
Figures 1, 4:
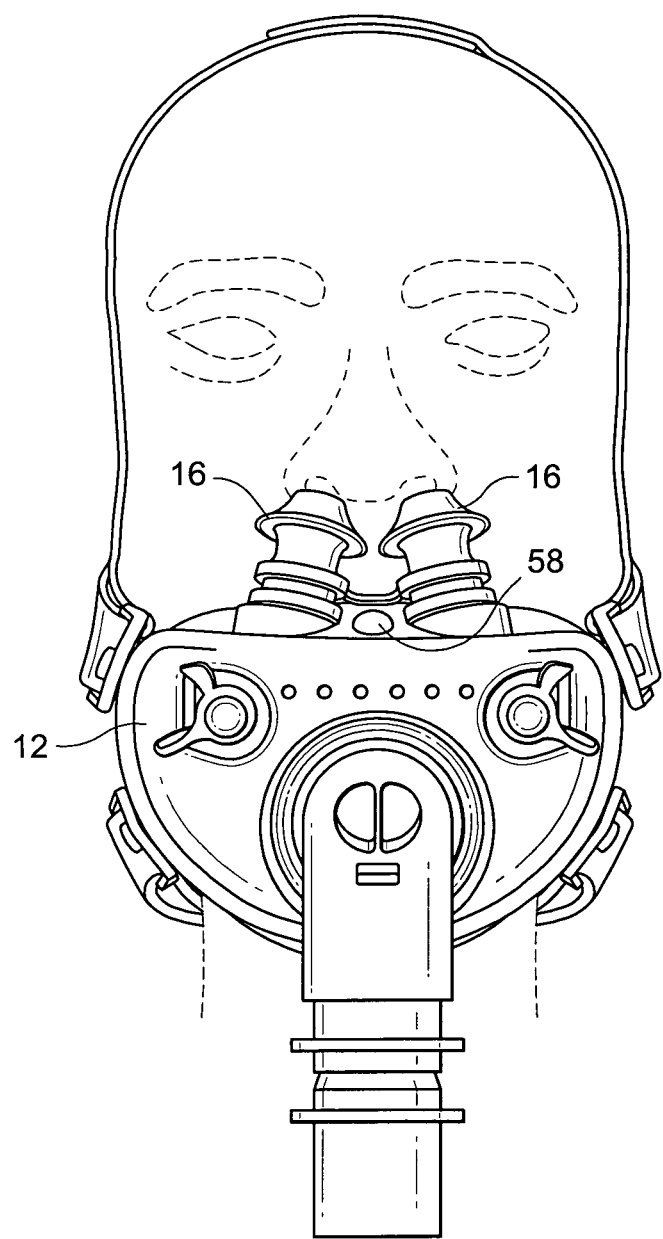
Figures 2, 4:
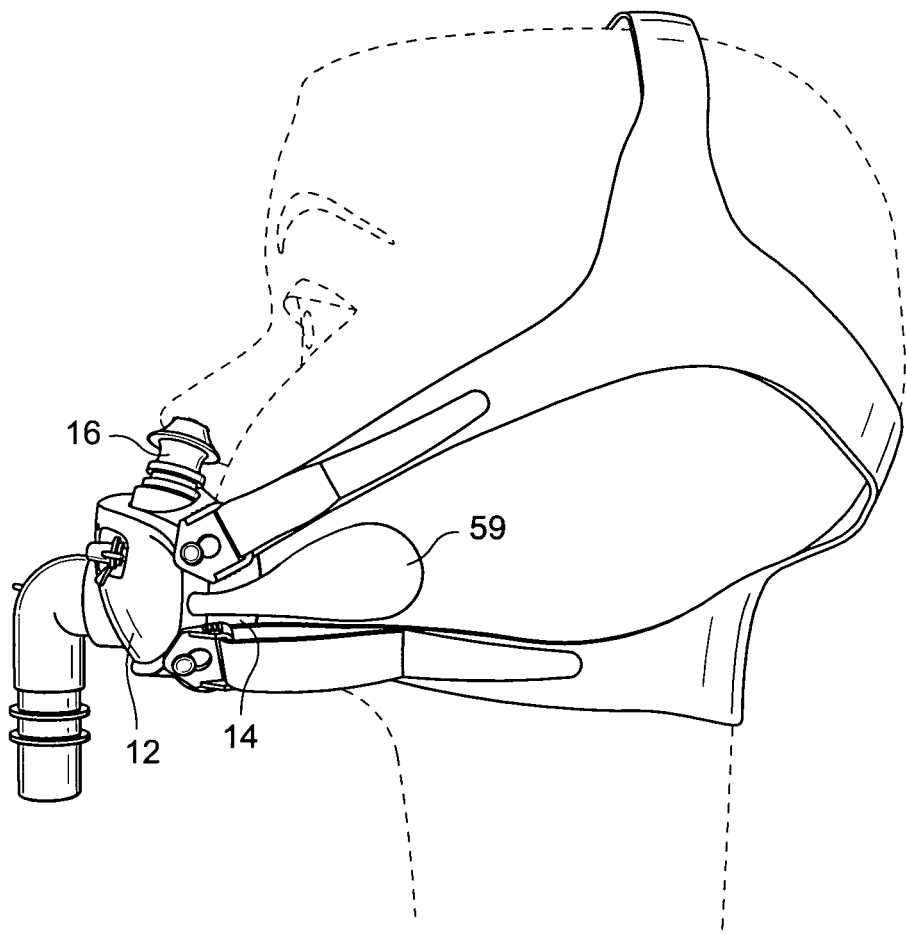
Figures 1, 5:
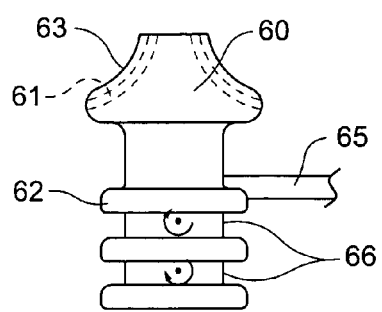
Figures 2, 5:
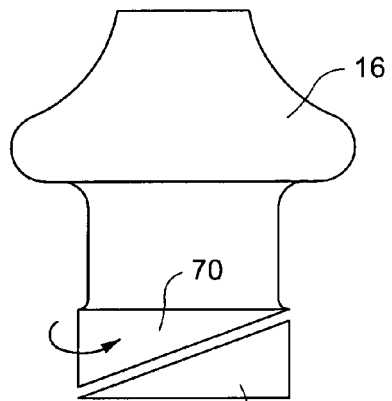
Figures 1, 3, 5:
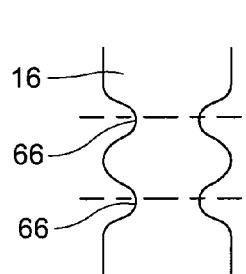
Figures 2, 3, 5:
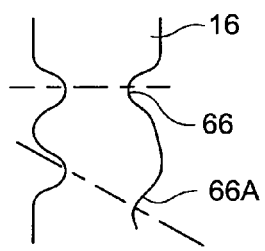
Figures 3, 5:
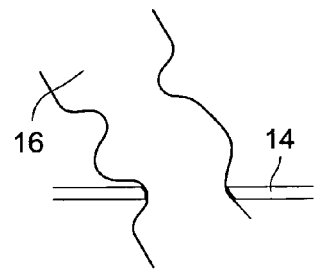
Figures 4, 5:
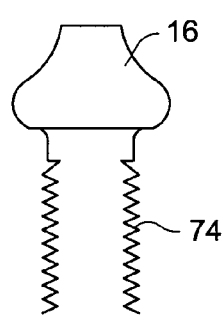
Figure 5:
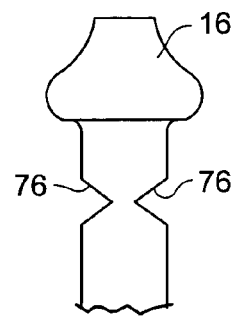
Figures 5, 6:
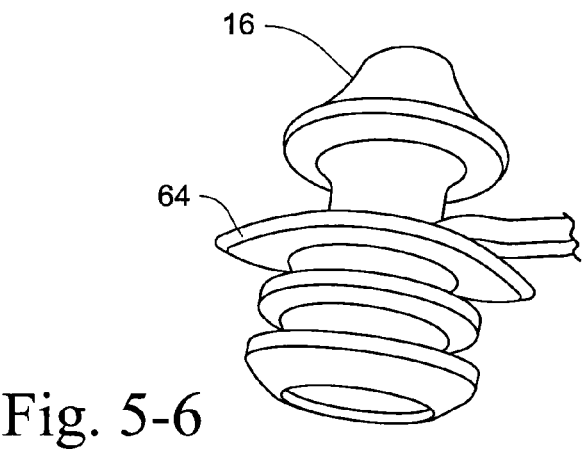
Figures 5, 6, 7:
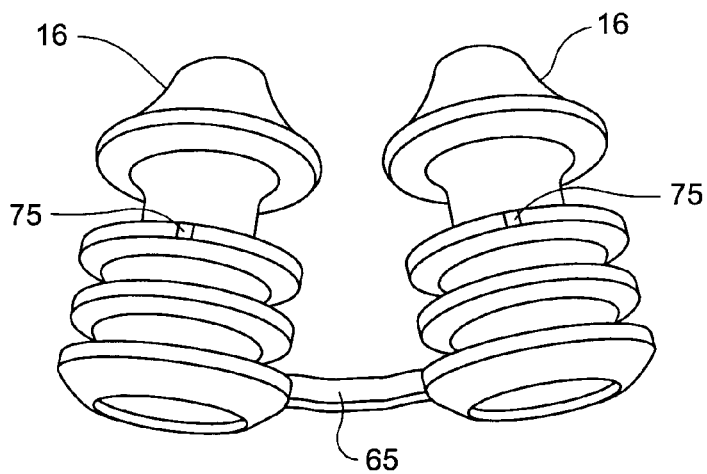
Figures 3, 6:
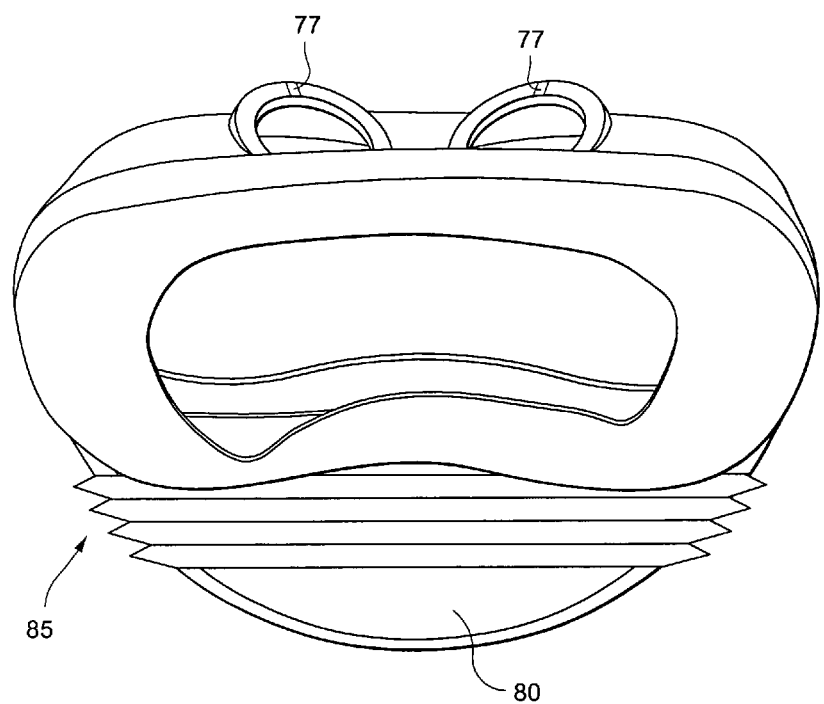
Figures 1, 7:
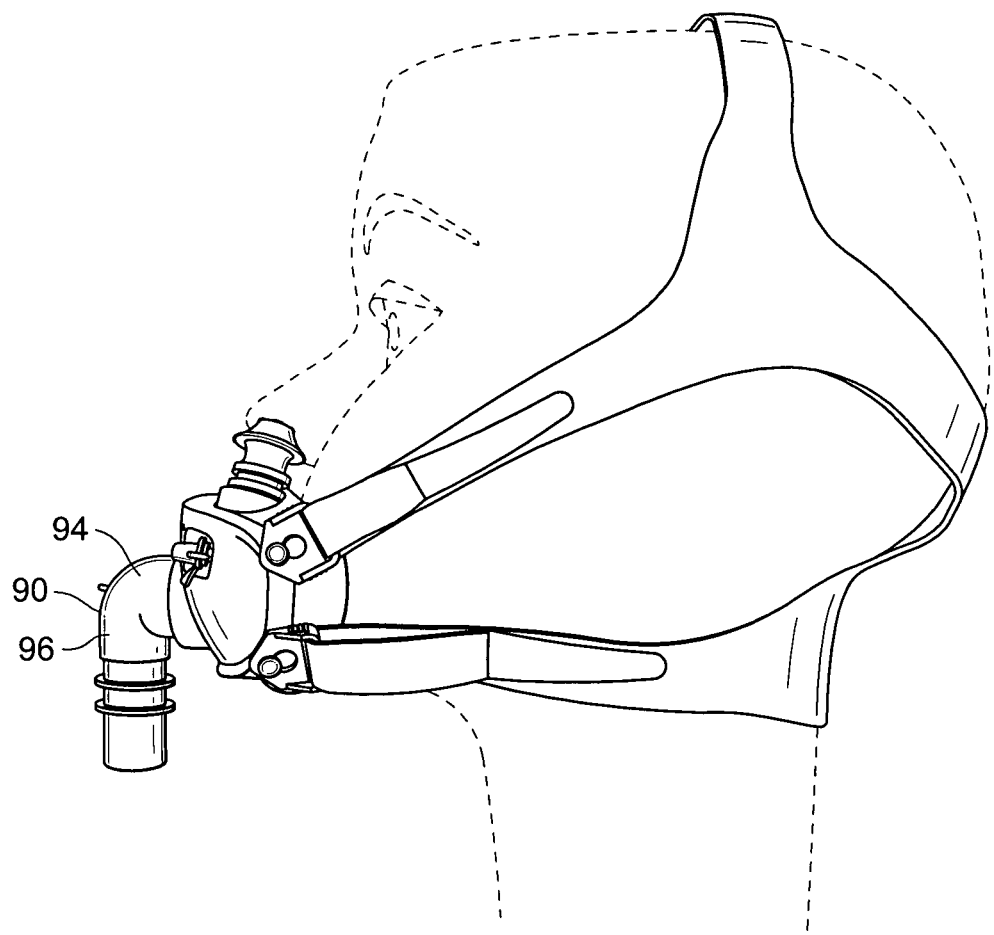
Figures 2, 7:
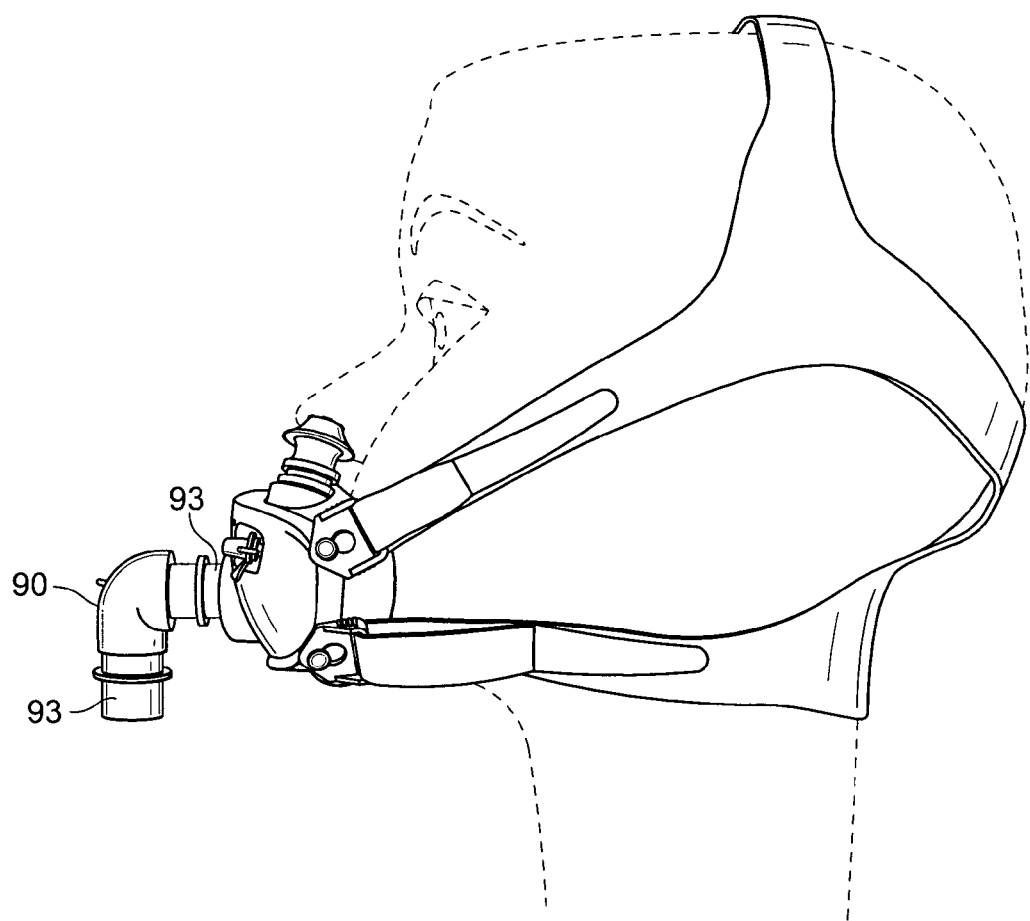
Figures 3, 7:
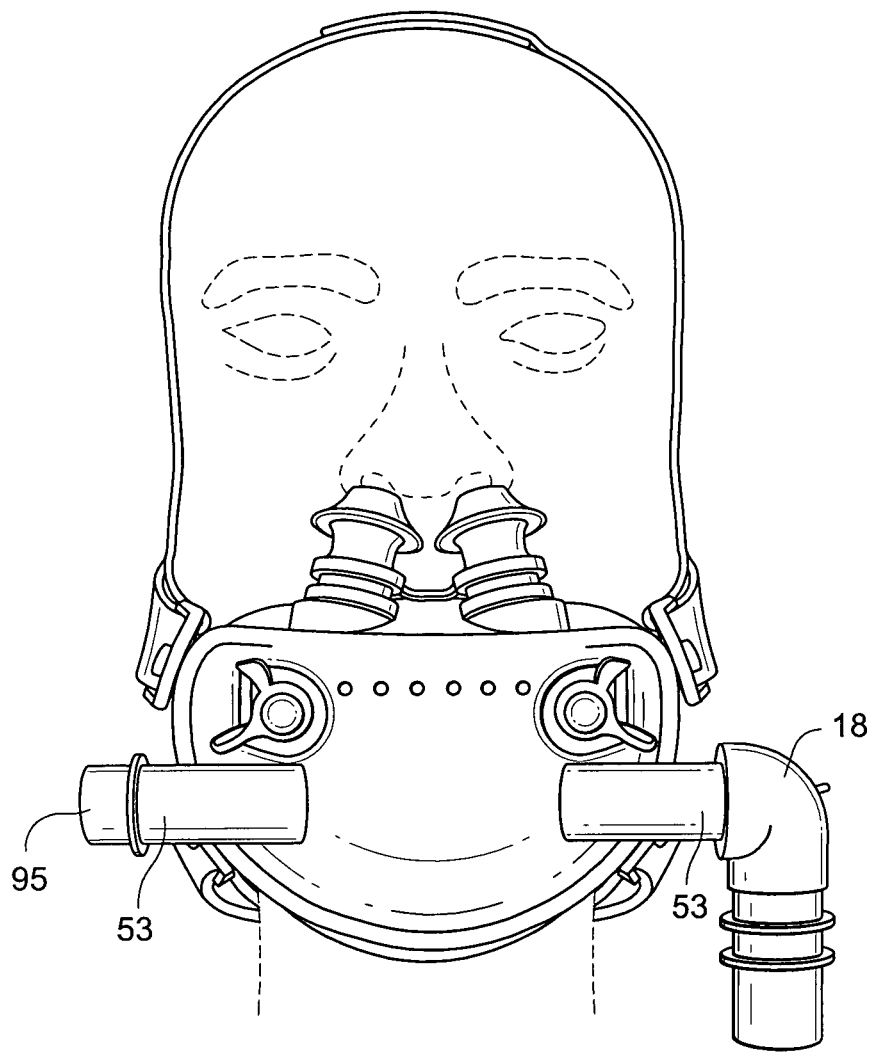
Figures 1, 8:
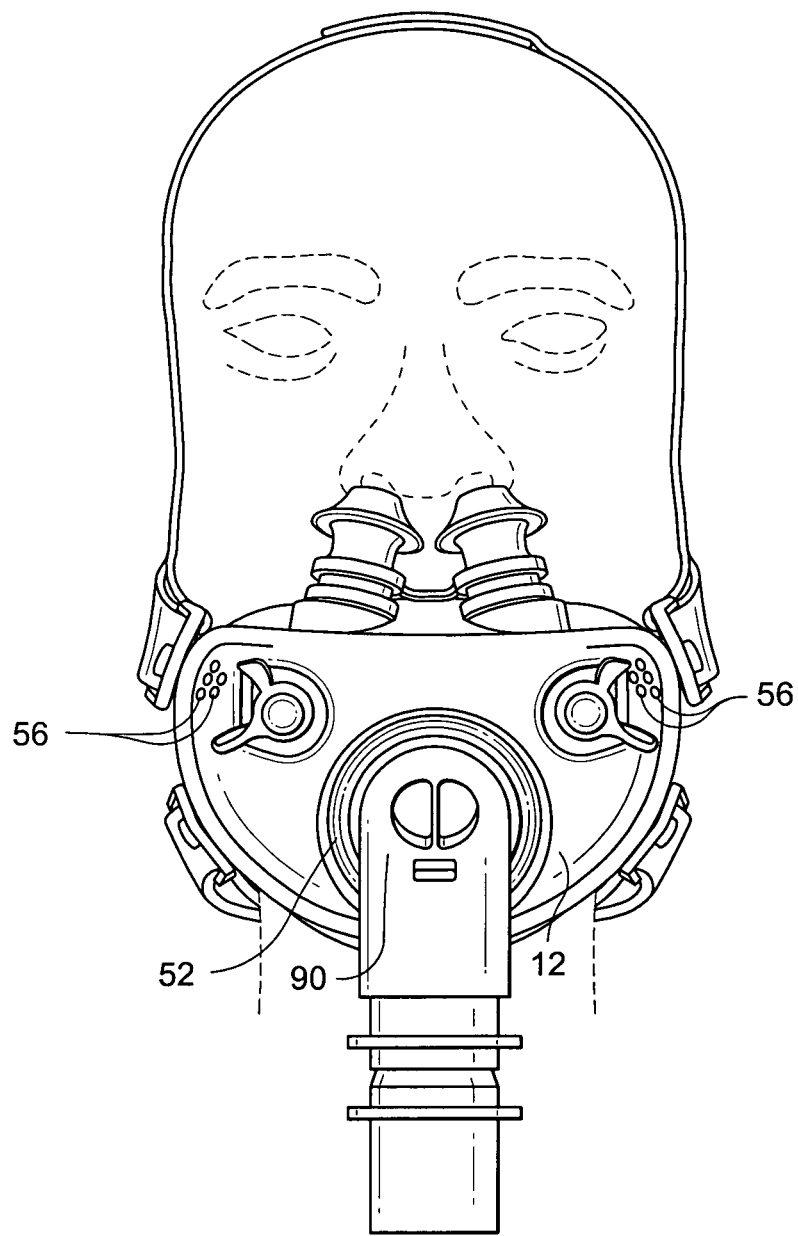
Figures 2, 8:
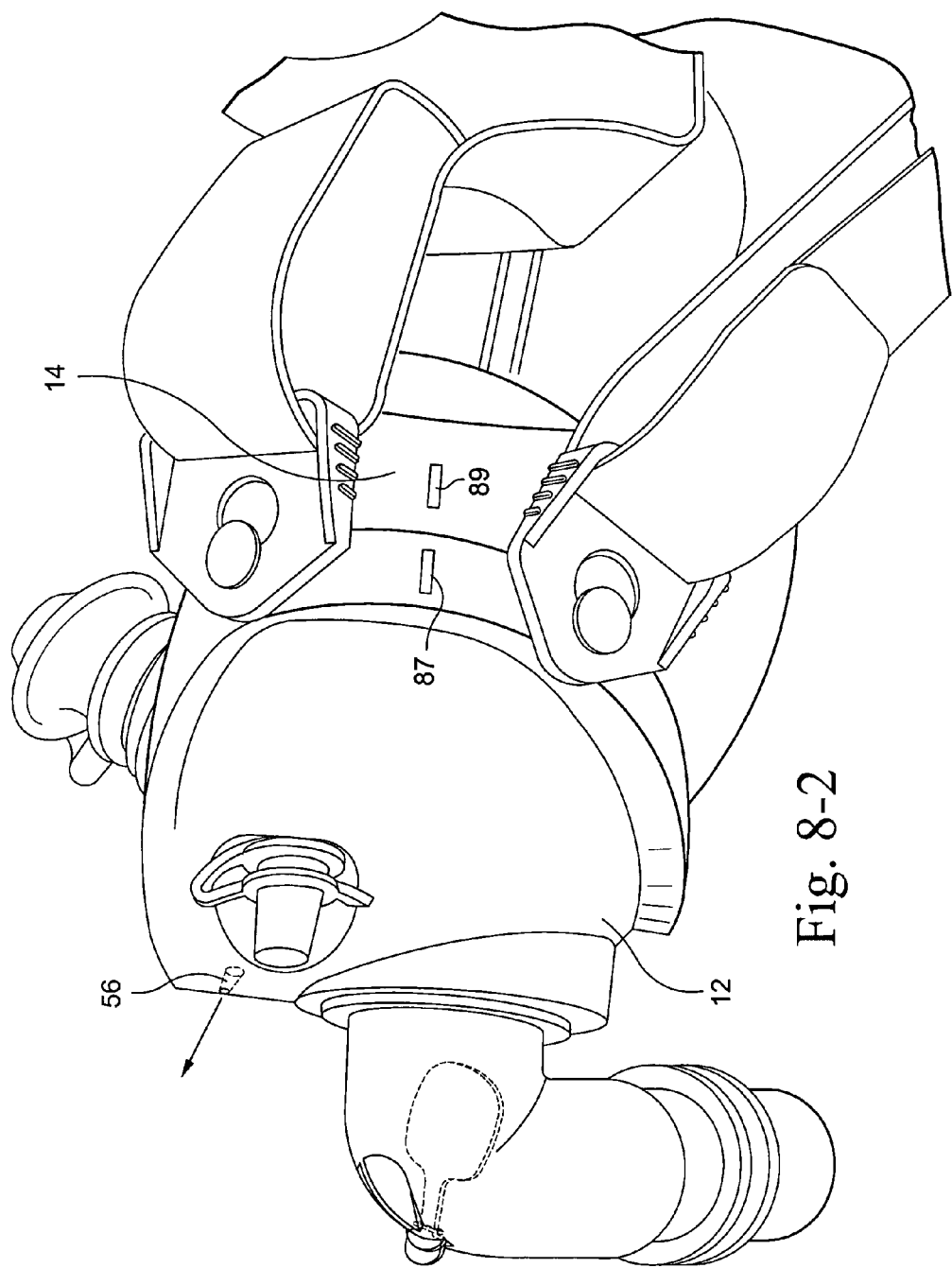
Figures 3, 8:
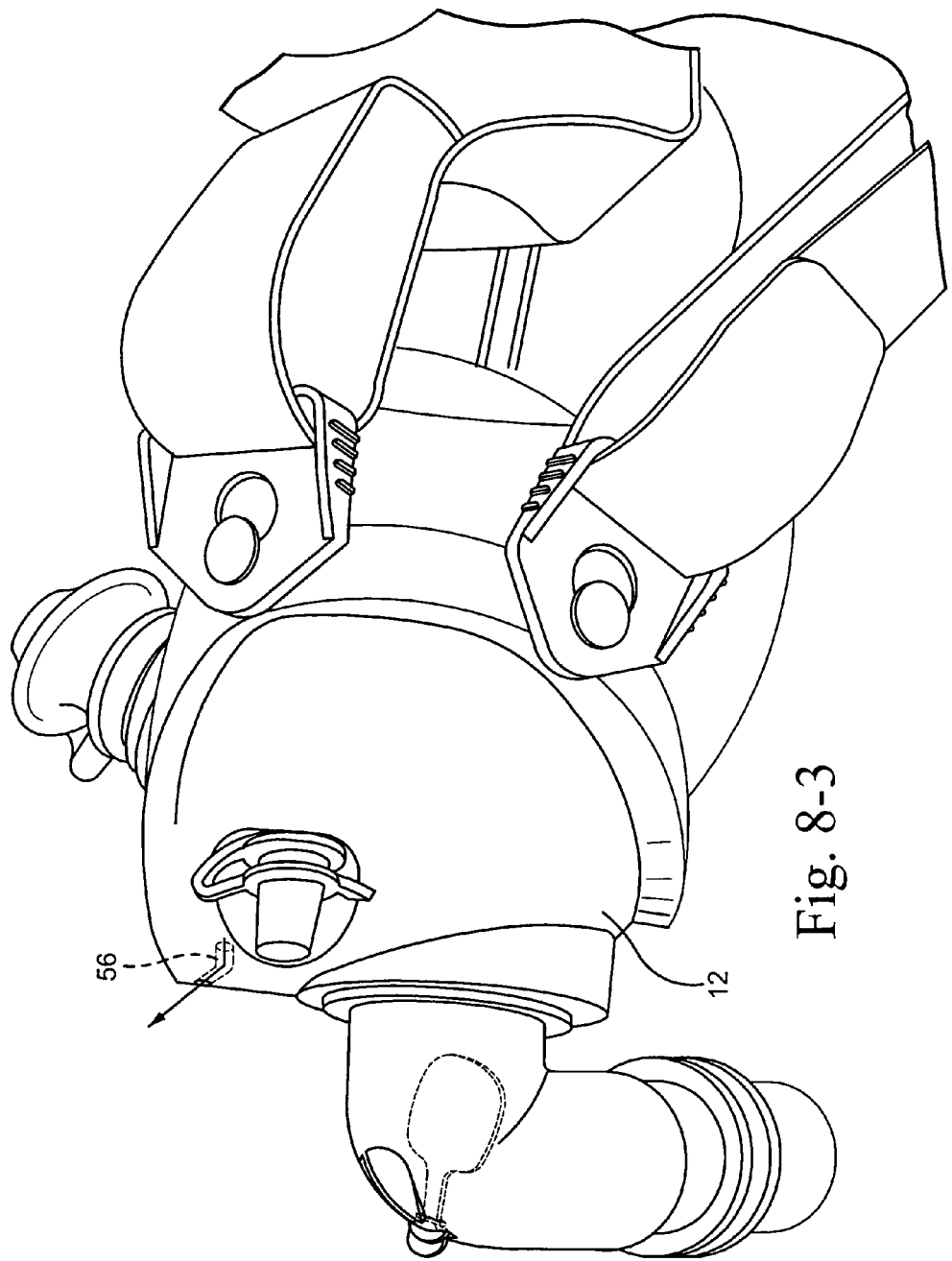
Figures 4, 8:
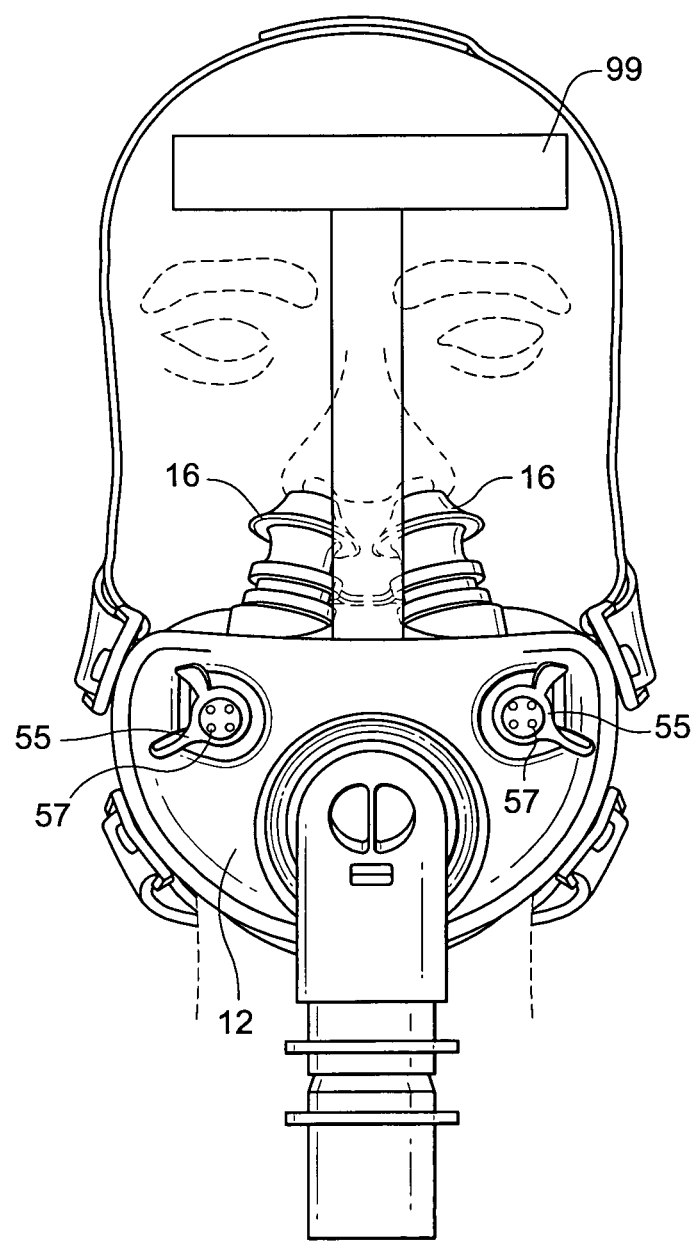

In an alternative embodiment, as shown in FIG. 5-7, the connecting bar 65 joining the prongs 16 may be provided at the bottom edge of the prong base portions, e.g., to avoid patient's septum. Such an arrangement is disclosed in PCT Application No. PCT/AU2006/000770, filed Jun. 6, 2006, which is incorporated herein by reference in its entirety.

In an alternative embodiment, as shown in FIG. 5-8, each prong 16 may include one or more stiffening members 78.

2.5 Cushion

The cushion 14 of the HYBRID™ mask 10 includes a chin portion or chin flap 80, an upper surface defining two portals 68 adapted to mount respective nasal prongs 16, a face-contacting portion having a double wall configuration (e.g., membrane 82 and undercushion 84), and a non-face-contacting portion having a leading edge 86 adapted to engage a groove 88 provided to the frame 12 to secure the cushion 14 to the frame 12 (e.g., see FIGS. 1-9 to 1-11).

2.5.1 Cushion Profile

As shown in FIG. 6-1-1, the profile of the HYBRID™ cushion 14 is generally J-shaped. In an alternative embodiment, as shown in FIG. 6-1-2, the cushion profile may have a question-mark or sickle shape. The question-mark or sickle shape may provide the cushion with greater range of movement or flexibility towards the patient's face in use. An exemplary cushion with a question-mark or sickle shape profile is described in PCT Publication No. WO 2006/074513, published Jul. 20, 2006, which is incorporated herein by reference in its entirety.

2.5.2 Gusset

In an alternative embodiment, as shown in FIG. 6-2, the cushion 14 may include a gusset arrangement 85 to provide a reduced height profile, increased stability, better fit to the patient's face, and/or a reduced visual impact.

An exemplary cushion with a gusset is described in U.S. patent application Ser. No. 10/655,622, filed Sep. 5, 2003, which is incorporated herein by reference in its entirety.

2.5.3 Cushion to Frame Interface

The leading edge of the HYBRID™ cushion is a substantially flat wall, which may easily disengage from the groove in the frame, e.g., especially when greasy. In an alternative embodiment, a lip, lug, bead, and/or or rib may be provided to the leading edge of the cushion to better retain the cushion to the frame. Such retaining structures are disclosed in U.S. patent application Ser. No. 10/390,682, filed Mar. 19, 2003, which is incorporated herein by reference in its entirety.

2.5.4 Other Cushion Alternatives

In an alternative embodiment, the face-contacting portion may include more than two walls, e.g., membrane 82 and two or more undercushions 84.

In an alternative embodiment, the cushion may have a preload to provide a sealing force.

In an alternative embodiment, one or more alignment indicators may be added to the cushion 14 and/or frame 12 to aid alignment of the cushion 14 with respect to the frame 12. For example, FIG. 8-2 illustrates an alignment indicator 87 provided to the frame 12 that is adapted to be aligned with a respective alignment indicator 89 provided to the cushion 14. Such alignment indicators are also disclosed in U.S. patent application Ser. No. 10/390,682, filed Mar. 19, 2003, which is incorporated herein by reference in its entirety.

In an alternative embodiment, the chin flap 80 may be adjustable, e.g., indexed or incremental adjustment. In an embodiment, as shown in FIG. 6-3, the chin flap may include a bellows arrangement 85 to allow movement of the chin in use.

In an alternative embodiment, the chin flap 80 may include multiple chin supports.

In an alternative embodiment, cheek supports may be provided to the cushion 14, e.g., cheek wings, such as the cheek support shown in FIG. 4-2.

In an alternative embodiment, the cushion may be configured or shaped to accommodate the patient's septum and/or nasal bridge. Such cushion arrangements are disclosed in U.S. patent application Ser. No. 10/390,682, filed Mar. 19, 2003, and U.S. Pat. No. 6,112,746, each of which is incorporated herein by reference in its entirety.

2.6 Elbow Assembly

The elbow assembly 18 of the HYBRID™ mask 10 includes an elbow 90 and a swivel coupling 92 provided to the elbow 90. The elbow 90 includes a first portion 94 attachable to the frame 12 and a second portion 96 attachable to the swivel coupling 92. Also, the elbow 90 includes a port 98 that is selectively closed by an anti-asphyxia valve 99 (e.g., see FIGS. 1-3 to 1-5 and 1-9).

2.6.1 Shortened Length

As shown in FIGS. 1-3 to 1-5, the second portion 96 of the HYBRID™ elbow 90 is substantially longer than the first portion 94. In an alternative embodiment, as shown in FIG. 7-1, the second portion 96 of the elbow 90 may be shortened to improve stability.

2.6.2 Tolerances

In the commercial embodiment of the HYBRID™ mask 10, excessive noise is caused by significant leakage through the elbow to frame interface. In an alternative embodiment, the manufacturing tolerances of the elbow 90 and/or frame 12 may be improved to reduce noise caused by leak through the elbow to frame interface.

2.6.3 Other Elbow Assembly Alternatives

In an alternative embodiment, as shown in FIG. 7-2, a relatively short swivel coupling 93 may be provided to each end of the elbow 90 to allow greater flexibility.

In another alternative embodiment, a swivel coupling 92 may be provided over the elbow 90 to reduce the size of the elbow 90.

In another alternative embodiment, the elbow to frame connection may include a ball joint arrangement.

In another alternative embodiment, the frame 12 may include two gas entry ports 53, e.g., one on each side of the frame as shown in FIG. 7-3. In use, one of the ports may be provided with a plug 95 and the other of the ports may be provided with an elbow assembly 18. The positions of the plug and the elbow assembly may be interchanged, according to preference. Thus, the mask 10 may be configurable between two different configurations.

In another alternative embodiment, the elbow assembly may be constructed of materials to prevent "squeaking" in use.

In another embodiment, the swivel coupling may permanently attach to the elbow with a snap-fit, e.g., to prevent separation.

In another embodiment, the elbow may be structured to facilitate removal of the anti-asphyxia valve, e.g., for cleaning so that the mask is suitable for use by multiple patients. For example, the anti-asphyxia valve may be attached to a removable clip member that is removably attachable to the elbow. Exemplary anti-asphyxia valve assemblies are disclosed in PCT Publication No. WO 2007/045008, published Apr. 26, 2007, which is incorporated herein by reference in its entirety.

2.7 Vent Holes

The HYBRID™ frame 12 includes six vent holes 56 for $CO_2$ washout. The vent holes 56 are positioned above the gas entry port 52 and aligned along a horizontal axis (e.g., see FIGS. 1-5 and 1-9).

2.7.1 Size and Number

In an alternative embodiment, the size of each vent hole 56 may be smaller and the number of vent holes 56 provided to the frame 12 may be increased, e.g., greater than six vent holes (e.g., 6-60 vent holes). Exemplary vent arrangements are disclosed in U.S. Pat. No. 6,581,594 and PCT Application Nos. PCT/AU2006/000770, filed Jun. 6, 2006, and PCT/AU2006/001507, filed Oct. 13, 2006, each of which is incorporated herein by reference in its entirety.

2.7.2 Positioning

In an alternative embodiment, as shown in FIG. 8-1, the vent holes 56 may be moved away from the gas entry port 52 and elbow 90 connected thereto. This vent arrangement may provide less interference with the elbow 90 and therefore less noise in use. Such a vent arrangement is disclosed in PCT Application No. PCT/AU2006/000770, filed Jun. 6, 2006, which is incorporated herein by reference in its entirety.

2.7.3 Vent Hole Direction

In the commercial embodiment of the HYBRID™ mask 10, the vent holes 56 direct washout gas along a generally horizontal plane or axis of the frame 12. In an alternative embodiment, as shown in FIG. 8-2, the vent holes 56 may be configured to direct washout gas at an angle with respect to the horizontal axis of the frame 12. In an embodiment, a grommet may be provided to one or more of the vent holes to direct washout gas at an angle.

In another alternative embodiment, as shown in FIG. 8-3, the vent holes 56 may be configured such that washout gas enters each vent hole along one path and exits each vent hole along another path.

2.7.4 Other Vent Alternatives

In an alternative embodiment, one or more vent holes for $CO_2$ washout may be provided in the base of each nasal prong 16 and/or in the cushion 14.

In another alternative embodiment, as shown in FIG. 8-4, one or more vent holes for $CO_2$ washout may be provided to the port cap 55 that covers a respective supplemental oxygen port 54 of the frame 12, e.g., vent and port cap integrated into one elastomeric component.

In another alternative embodiment, the two port cap 55 may be tethered to one another, e.g., double ports cap. Such an arrangement is disclosed in U.S. Pat. No. 6,439,230, which is incorporated herein by reference in its entirety.

2.8 Miscellaneous

The following embodiments describe additional improvements and/or alternative arrangements of the HYBRID™ mask.

2.8.1 Forehead Support

In an alternative embodiment, as schematically shown in FIG. 8-4, a forehead support 99 may be provided to the HYBRID™ mask 10 to provide a support and stability mechanism between the mask and the patient's forehead. Exemplary forehead support arrangements are disclosed in U.S. Pat. Nos. 6,119,693 and 6,532,961 and PCT Application No. PCT/AU2006/000037, filed Jan. 12, 2006, each of which is incorporated herein by reference in its entirety.

In an embodiment, the forehead support may include forehead pads that extend up and around the outside of the patient's eyes. Exemplary forehead pads are disclosed in U.S. patent application Ser. No. 10/655,595, filed Sep. 5, 2003, which is incorporated herein by reference in its entirety.

In another embodiment, the forehead support may include a nose support adapted to engage the nose and provide a support and stability mechanism between the mask and the patient's nose.

In another embodiment, the forehead support may include a cheek support adapted to engage the patient's cheeks and provide a support and stability mechanism between the mask and the patient's cheeks, e.g., such as the cheek support shown in FIG. 4-2.

2.8.2 Other Alternatives

In an alternative embodiment, the HYBRID™ mask 10 may include an intra-oral bite or dental insert provided within the patient's mouth. In an embodiment, the insert may constitute a mandibular advancement device structured to advance the position of the patient's lower jaw. An exemplary mandibular advancement device is disclosed in PCT Application No. PCT/AU2006/001095, filed Aug. 2, 2005, which is incorporated herein by reference in its entirety.

In another alternative embodiment, the frame 12, cushion 14, nasal prongs 16, and/or headgear 20 of the HYBRID™ mask 10 may be constructed of a malleable material to allow bending for conformance to the patient's head and/or face, e.g., conform mask to suit different faces.

In another alternative embodiment, the frame 12 and/or cushion 14 may include an articulating feature that allows the jaw to move in use. The articulating feature may be adjustable and lockable.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. A mask comprising:
a frame;
a facial and nasal interface provided to the frame; and
headgear provided to the frame to maintain the mask in a desired position on the patient's face,
the headgear including at least one strap and a buckle provided to the strap, the buckle including an opening adapted to receive a mushroom-shaped post provided on the frame,
wherein the opening and the mushroom-shaped post both comprise keyed portions structured to rotationally lock the mushroom-shaped post when the keyed portions of the opening and the mushroom-shaped post are engaged.

2. The mask according to claim 1, wherein the buckle is rotatable relative to the mushroom-shaped post to set a desired position, and when the desired position is set, the buckle is rotationally locked against the mushroom-shaped post.

3. The mask according to claim 1, wherein a perimeter of the opening is defined by a first portion and a second portion, the opening and the mushroom-shaped post being structured so that a lateral movement of the mushroom-shaped post from the first portion to the second portion rotationally locks the mushroom-shaped post within the opening.

4. The mask according to claim 3, wherein the mushroom-shaped post is provided on a lower part of the frame, and the first portion of the opening is larger than the second portion of the opening to allow the buckle to be disengaged and removed from the mushroom-shaped post.

5. The mask according to claim 3, wherein the mushroom-shaped post is structured so that the mushroom-shaped post cannot be received by the second portion of the opening without first being received by the first portion of the opening.

6. The mask according to claim 5, wherein the first portion of the opening is larger than the second portion of the opening.

7. The mask according to claim 6, wherein the opening is structured so that when rotation of the buckle with respect to the mushroom-shaped post is prevented by an interaction between the opening and the mushroom-shaped post, the mushroom-shaped post is positioned completely within the second portion.

8. The mask according to claim 7, wherein the second portion of the opening is the keyed portion of the opening.

9. The mask according to claim 3, wherein the first portion is structured to receive the mushroom-shaped post and permit rotation of the buckle with respect to the mushroom-shaped post while the mushroom-shaped post is within the first portion and the second portion is structured to engage the mushroom-shaped post and prevent rotation of the buckle with respect to the mushroom-shaped post when the mushroom-shaped post is engaged with the second portion.

10. The mask according to claim 9, wherein the first portion is structured to fully receive the mushroom-shaped post when the mushroom-shaped post is in any rotational orientation.

11. The mask according to claim 10, wherein the second portion is structured to fully receive the mushroom-shaped post from the first portion only when the mushroom-shaped post is rotationally oriented at certain discrete orientations.

12. The mask according to claim 3, wherein the first portion of the opening is structured to permit rotation of the mushroom-shaped post within the opening and the second portion of the opening is structured to prevent rotation of the mushroom-shaped post within the opening.

13. The mask according to claim 1, wherein the opening and the post are structured so that when the post is received within the opening, movement of the buckle relative to a front portion of the frame rotationally locks the post within the opening.

14. A mask comprising:
a frame;
a facial and nasal interface provided to the frame; and
a lotion dispenser proximate to the nasal interface and adapted to dispense lotion retained within the dispenser for lubricating and/or moisturizing the facial and/or nasal interface,
wherein the frame includes the lotion dispenser.

15. The mask according to claim 14, wherein the facial interface includes a cushion adapted to form a seal around an exterior of the patient's mouth in use.

16. The mask according to claim 14, wherein the nasal interface includes nasal prongs adapted to form a seal with the patient's nasal passages in use.

17. The mask according to claim 16, wherein the lotion dispenser is positioned between the prongs.

18. The mask according to claim 14, further comprising headgear provided to the frame to maintain the mask in a desired position on the patient's face.

19. The mask according to claim 14, wherein the frame includes a gas entry port adapted to connect to an elbow assembly.

20. The mask according to claim 14, wherein the frame includes supplemental oxygen ports.

21. The mask according to claim 14, wherein the frame includes vent holes for $CO_2$ washout.

22. The mask according to claim 14, wherein the lotion dispenser comprises a pocket from which said lotion is dispensed.

23. The mask according to claim 22, wherein the pocket comprises a reservoir on the frame.

24. The mask according to claim 14, wherein the lotion dispenser is centrally located on the frame.

25. A mask comprising:
a frame;
a cushion provided to the frame and adapted to form a seal around an exterior of the patient's mouth in use; and
nasal prongs provided to the cushion and adapted to form a seal with the patient's nasal passages,
wherein each of the nasal prongs is adapted to change an angle at which its own longitudinal axis extends with respect to the cushion by rotating around said longitudinal axis.

26. The mask according to claim 25, wherein each of the nasal prongs includes a sloped end that engages a sloped base provided to the cushion such that rotation of the nasal prong is adapted to rotate the sloped end relative to the sloped base which changes the angle at which the prong extends with respect to the cushion.

27. The mask according to claim 26, wherein the sloped end of each nasal prong is sloped with respect to the nasal prong's longitudinal axis and the sloped base is sloped with respect to a surface of the cushion surrounding the base, and rotation of the nasal prong is adapted to rotate the sloped end relative to the sloped base which changes the angle at which the prong extends with respect to the surface of the cushion surrounding the base.

28. The mask according to claim 25, wherein each prong includes a stalk extending from the cushion and a head provided to a distal end of the stalk, the stalk being adapted to rotate to change the angle at which a longitudinal axis of the stalk extends relative to the cushion.

29. The mask according to claim 25, wherein at least one of the prongs includes an alignment indicator to aid in alignment of the prong relative to the cushion.

* * * * *